(12) United States Patent
Virden

(10) Patent No.: US 12,042,615 B2
(45) Date of Patent: Jul. 23, 2024

(54) ATRAUMATIC SUBCUTANEOUS MEDICATION DELIVERY

(71) Applicant: Charles P. Virden, Reno, NV (US)

(72) Inventor: Charles P. Virden, Reno, NV (US)

(73) Assignee: VITALTE LIFESCIENCES INC., Reno, NV (US)

( * ) Notice: Subject to any disclaimer, the term of this patent is extended or adjusted under 35 U.S.C. 154(b) by 699 days.

(21) Appl. No.: 16/997,803

(22) Filed: Aug. 19, 2020

(65) Prior Publication Data

US 2021/0128899 A1 May 6, 2021

Related U.S. Application Data

(63) Continuation-in-part of application No. PCT/US2019/019031, filed on Feb. 21, 2019, which is a continuation of application No. 15/901,821, filed on Feb. 21, 2018, now Pat. No. 11,406,806, and a continuation of application No. 15/901,837, filed on Feb. 21, 2018, now Pat. No. 10,856,907.

(51) Int. Cl.
  *A61M 37/00* (2006.01)
  *A61B 17/34* (2006.01)

(52) U.S. Cl.
  CPC ..... *A61M 37/0069* (2013.01); *A61B 17/3421* (2013.01); *A61B 2017/3456* (2013.01); *A61B 17/3468* (2013.01)

(58) Field of Classification Search
  CPC ............ A61M 37/0069; A61M 31/002; A61M 31/007; A61B 17/3421; A61B 17/3468
  See application file for complete search history.

(56) References Cited

U.S. PATENT DOCUMENTS 3,491,756 A * 1/1970 Bentov ............... A61M 5/32
                                                    604/164.01
3,921,632 A 11/1975 Bardani
4,535,773 A 8/1985 Yoon
(Continued)

FOREIGN PATENT DOCUMENTS

WO    1996001132 A1    1/1996

OTHER PUBLICATIONS

Chew, Steph, Basic Laparoscopic Technique and Advanced Endoscopic Suturing: a Practical Guidebook, 2001, Singapore University Press/World Scientific, p. 19 (Year: 2001).*
(Continued)

*Primary Examiner* — Nilay J Shah
(74) *Attorney, Agent, or Firm* — Kerr IP Group, LLC

(57) ABSTRACT

An atraumatic trocar apparatus, kit, and method of use are described. The atraumatic trocar includes a cannula and an obturator with an anterior rounded tip and an opening proximate to the anterior rounded tip. The atraumatic trocar is assembled by passing the obturator through an interior passage of a tubular cannula body of the cannula. The assembled atraumatic trocar is used to probe an incision, while delivering a hydrodissecting fluid through the opening to create a fluid channel, to reach a delivery site within subcutaneous tissue. The obturator is removed from the cannula and two or more medication pellets loaded within the interior passage. The obturator is used to push the medication pellets through the interior passage to the delivery site and deposit the medication pellets within the subcutaneous tissue.

20 Claims, 16 Drawing Sheets

(56) References Cited

U.S. PATENT DOCUMENTS

| | | | |
|---|---|---|---|
| 5,487,739 A * | 1/1996 | Aebischer | B01J 13/02 |
| | | | 604/93.01 |
| 5,928,130 A | 7/1999 | Schmidt | |
| 6,210,315 B1 | 4/2001 | Andrews et al. | |
| 6,241,734 B1 * | 6/2001 | Scribner | A61B 17/8833 |
| | | | 606/93 |
| 6,358,195 B1 | 3/2002 | Green et al. | |
| 6,402,677 B1 | 6/2002 | Jacobs | |
| 6,450,937 B1 | 9/2002 | Mercereau et al. | |
| 6,572,525 B1 | 6/2003 | Yoshizumi | |
| 6,656,106 B2 | 12/2003 | Schmidt | |
| 6,889,833 B2 * | 5/2005 | Seiler | A61M 37/0069 |
| | | | 206/370 |
| 7,344,519 B2 | 3/2008 | Wing | |
| 7,361,135 B2 | 4/2008 | Drobnik et al. | |
| 7,374,551 B2 | 5/2008 | Liang | |
| 7,479,150 B2 | 1/2009 | Rethy et al. | |
| 2001/0003149 A1 | 6/2001 | Utterberg | |
| 2003/0233101 A1 | 12/2003 | Lubock et al. | |
| 2004/0015133 A1 | 1/2004 | Karim | |
| 2005/0064046 A1 | 3/2005 | DiTrolio | |
| 2005/0203565 A1 | 9/2005 | Rethy | |
| 2006/0063962 A1 | 3/2006 | Drobnik | |
| 2006/0282042 A1 | 12/2006 | Walters | |
| 2008/0009792 A1 | 1/2008 | Henniges | |
| 2008/0033280 A1 | 2/2008 | Lubock | |
| 2009/0131908 A1 * | 5/2009 | McKay | A61B 17/3468 |
| | | | 604/60 |
| 2012/0253189 A1 | 10/2012 | Burbank | |
| 2012/0289987 A1 * | 11/2012 | Wilson | A61B 17/320783 |
| | | | 606/190 |
| 2013/0261596 A1 | 10/2013 | McKay | |
| 2014/0323808 A1 | 10/2014 | Evans | |
| 2014/0324090 A1 * | 10/2014 | Kafiluddi | A61B 17/3417 |
| | | | 606/186 |
| 2016/0175007 A1 | 6/2016 | Valbuena | |
| 2016/0296739 A1 | 10/2016 | Cleveland | |
| 2017/0049972 A1 * | 2/2017 | Persons | A61M 19/00 |
| 2017/0065805 A1 * | 3/2017 | Tutera | A61M 37/0069 |
| 2018/0085144 A1 | 3/2018 | McGillicuddy | |

OTHER PUBLICATIONS

Cavender, Richard K., Surgical Techniques: Subcutaneous Testosterone Pellet Implantation Procedure for Treatment of Testosterone Deficiency Syndrome, J Sex Med 2009; 6:21-24 (Jan. 8, 2009).

Conners, William et al., Outcomes with the "V" Implantation Technique vs. Standard Technique for Testosterone Pellet Therapy, J Sex Med 2011; 8:3465-3470 (Dec. 1, 2011).

*Vitalte Lifesciences Inc.* v. *Bonds Therapeutics LLC* Case No. 4:23-cv-00887 Plaintiff's Answer to Defendant's Counterclaims, Jul. 18, 2023 (5 pages).

*Vitalte Lifesciences Inc.* v. *Bonds Therapeutics LLC* Case No. 4:23-cv-00887-JG Defendant's Answer to Complaint, Jun. 27, 2023 (16 pages).

* cited by examiner

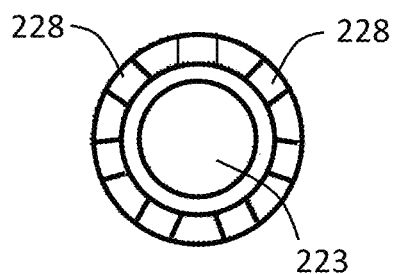
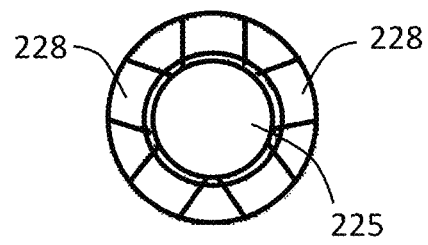
Figure 3A  Figure 3B
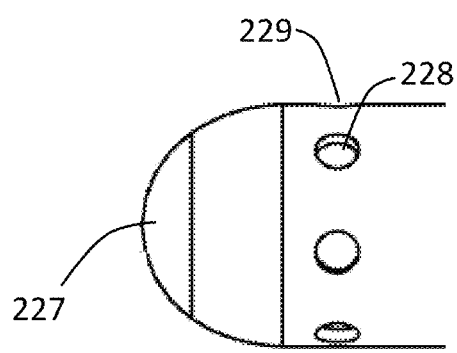
Figure 3C

Figure 7A
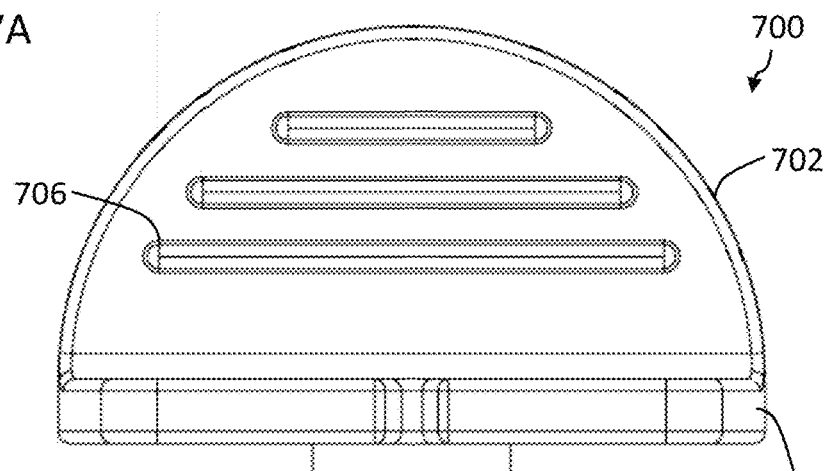
Figure 7B
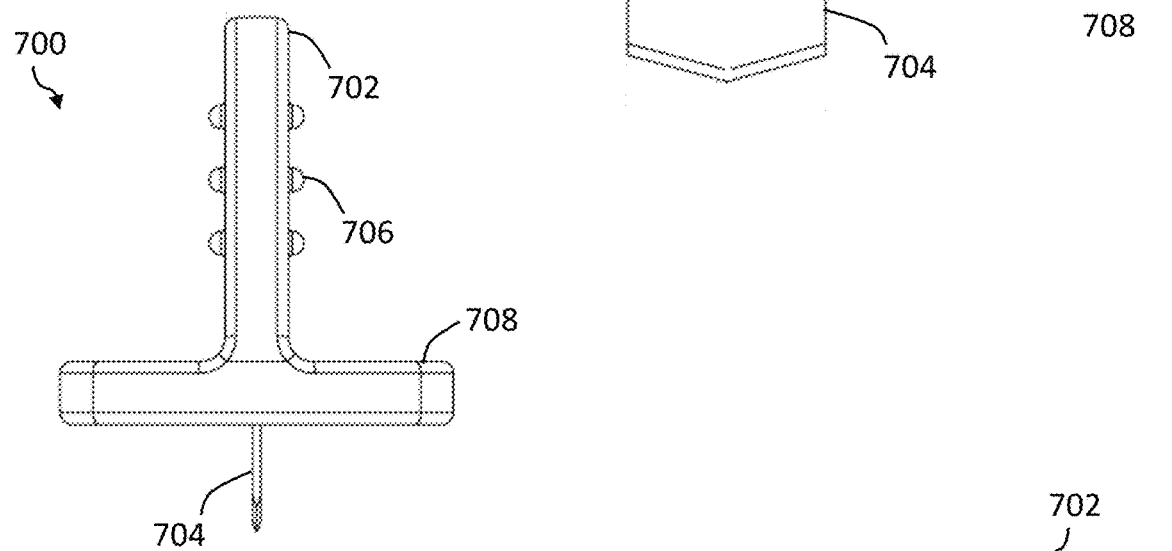
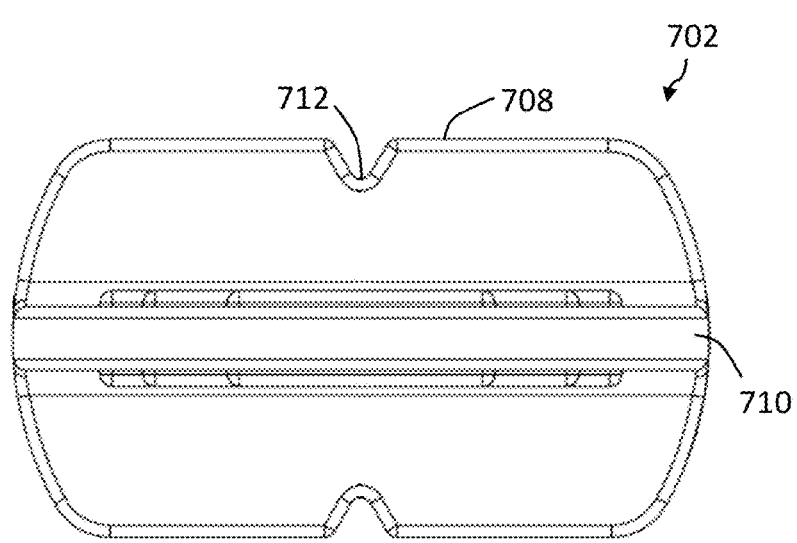
Figure 7C

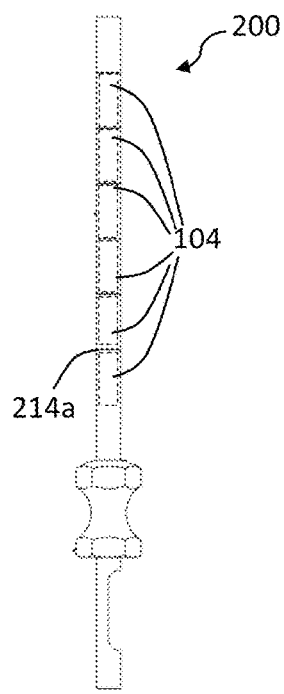
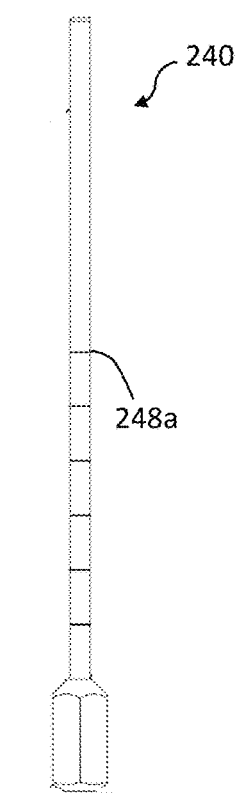
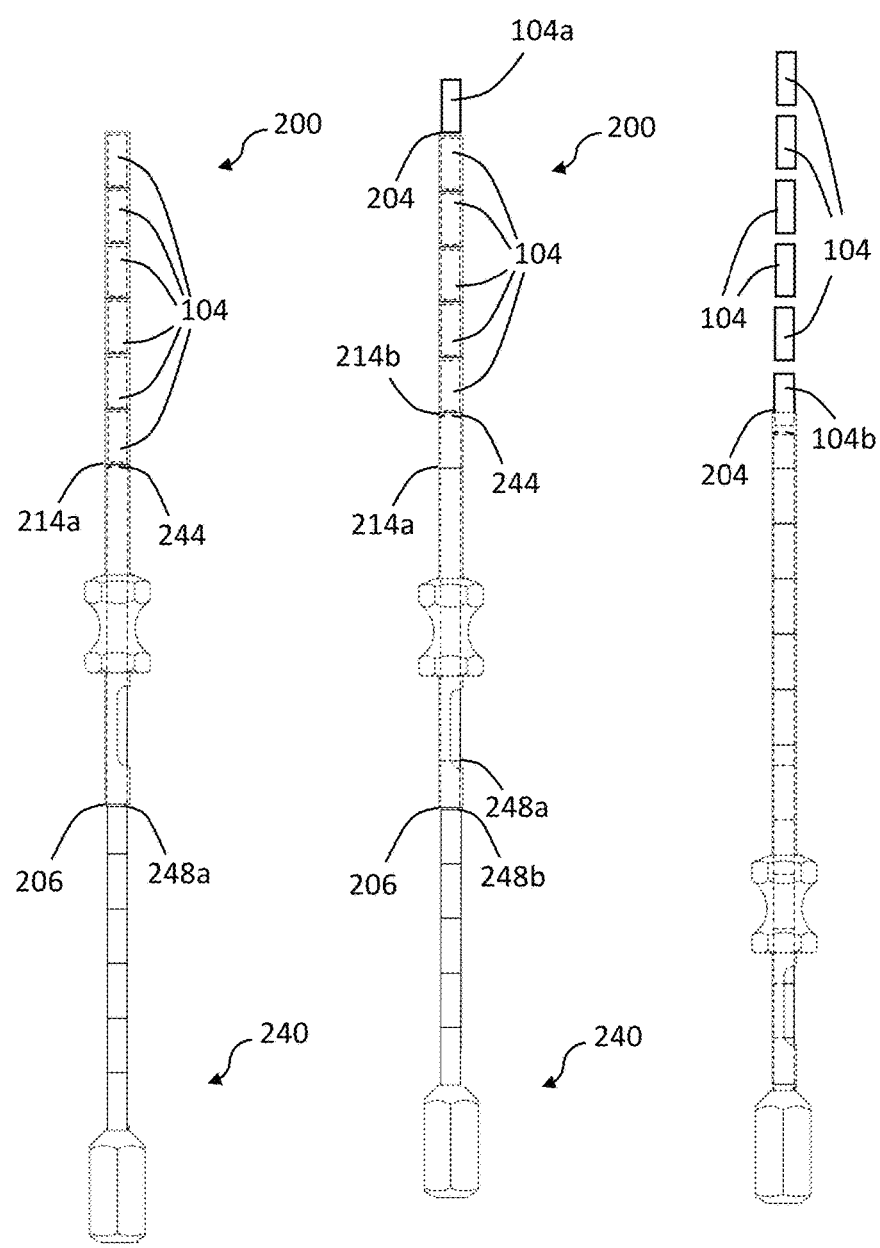
Figure 9A    Figure 9B    Figure 9C    Figure 9D

ATRAUMATIC SUBCUTANEOUS MEDICATION DELIVERY

CROSS-REFERENCE

This patent application is a continuation-in-part of international utility patent application PCT/US19/19031 filed on Feb. 21, 2019 entitled ATRAUMATIC SUBCUTANEOUS MEDICATION DELIVERY (published as WO 2019/165131); and is a continuation-in-part of utility patent application Ser. No. 15/901,837 (now U.S. Pat. No. 10,856,907) filed on Feb. 21, 2018 entitled ATRAUMATIC TROCAR MEDICATION DELIVERY METHOD; and is a continuation-in-part of utility patent application Ser. No. 15/901,821 (now U.S. Pat. No. 11,406,806) filed on Feb. 21, 2018 entitled ATRAUMATIC TROCAR APPARATUS, SYSTEM AND KIT. All patent application above are hereby incorporated by reference.

FIELD

The present disclosure relates to an atraumatic trocar apparatus, system, kit, and method of use. More particularly, the present disclosure relates to an atraumatic trocar apparatus, system and kit that includes a cannula that receives an insertion obturator having an anterior rounded tip.

BACKGROUND

Hormone therapies carry significant risks of adverse effects, which can be exacerbated from inconsistent or traumatic delivery as a result of a variety of hormone therapies. Pills may be forgotten by a patient and require relatively frequent pharmacy trips to refill prescriptions. Further, oral delivery can cause gastric distress, destruction of active ingredients (medications), and/or bypass initial metabolism in the liver. Patches may be unsightly, inconvenient, uncomfortable, removed too early, and fail to accommodate individuals requiring higher levels of hormone replacement. Creams may similarly be unsightly and inconvenient, as well as delivering inadequate levels of hormones, requiring repeated application, and allowing for missed applications. Injections require repeated and frequent trips to a doctor's office, and can be painful. Additionally, pill/oral, patch, cream, and injection therapies suffer inconsistent dosage delivery. Dosages of hormones delivered by these techniques tend to spike soon after injection, ingestion, or application, then taper quickly below efficacious medication levels.

Hormone therapies that utilize subcutaneous implants or "pellets" bypass the liver, do not affect clotting factors and do not increase the risk of thrombosis. For example, bioidentical testosterone delivered subcutaneously by pellet implant is cardiac protective, unlike oral, synthetic methyl-testosterone. Subcutaneous pellets have other practical advantages over patches, creams, and injections. Subcutaneous implants release medication consistently for months, freeing patients from frequent trips to the doctor as with injections, and eliminating adherence concerns typical to patient administered medications, such as creams and oral medications. Alternatively, implants or pellet therapy keep hormone levels consistent through the day and avoid rollercoaster-like effects from orally administered, topically administered, or injected hormones. The release of the drug from implanted pellets generally continue for a period of 3 to 6 months, or even up to 12 months, depending on the size and composition of the pellet.

Subcutaneously implanted hormone pellets may be smaller than a grain of rice or approximately the size of a marble and are implanted directly into the subcutaneous tissue, where they provide a slow continuous release of hormone(s) into the bloodstream. Typically, the pellets are implanted in the lower abdomen or buttocks, because of the generally large deposits of fat stored in these areas. The procedure is done in a physician's office with the use of a local anesthetic and a small incision for insertion of a trocar.

Trocar medical devices are commonly used to subcutaneously implant the hormone pellets. Trocar medical devices have been known to, and used by, physicians since at least the 19th century and commonly comprise a hollow tubular cannula and a rod-like obturator that fits snugly within the cannula. A wide variety of trocars exist that vary according to the medical purpose for which they are intended. Trocars are tailored for specific tasks, such as laparoscopic surgery or implant delivery.

With reference now to FIGS. 1A-C, there are shown the components of a prior art trocar apparatus for subcutaneous pellet insertion used in BIOTE® hormone replacement therapy. This prior art embodiment, includes an angled cutting edge formed from the angled orifice 102 of the cannula 100 and the angled tip 112 of the insertion obturator 110. The insertion obturator 110 is machined to fit within the cannula 100 when assembled into a trocar, such that the angled tip 112 of the insertion obturator 110 is flush with the angled orifice 102 of the cannula 100, forming a uniform cutting edge.

As the trocar is inserted into a small surface incision, the angled cutting edge is used to slice through the fatty and connective tissues impeding the passage of the trocar. Once inserted to a desired depth or insertion length, the insertion obturator 110 is removed from the cannula 100 and pellet(s) 104 are loaded into the cannula through a loading slot 106. A blunt delivery obturator 120 is then used in place of the angled insertion obturator to push the pellet(s) 104 through the angled orifice 102 of the cannula 100.

The delivery obturator 120 delivers the pellet(s) to a subcutaneous site. The angled orifice 102 facilitates delivery of multiple pellets 104 in a clumped orientation. With reference now to FIGS. 1D and 1E, a radial clump of pellets 130 is shown. This radial clump 130 is formed by rotating the cannula during extrusion/delivery of the pellets 104 from the angled orifice 102.

The body's primary response to the traumatic cutting insertion of the prior art beveled trocar results in inflamed tissue, lymph fluid, and clotted red blood cells. And the literature from the prior art systems teach that the inflammatory response triggered by traumatic trocar insertion of hormone pellets is critical to adequate hormone absorption.

However, prior art traumatic trocar insertion is painful and results in scarring. Additionally, traumatically inserted pellets may lead to infection or be extruded from the insertion site, which requires replacement with an additional traumatic insertion. Furthermore, the body's inflammatory response to the traumatic insertion causes patients significant pain in the days following insertion. Further still, the cutting and spearing motions used to insert angled or cutting edge trocars cause significant bruising immediately after insertion that lasts for days or weeks, and further cause scarring that may remain for a year or more. Further yet, this inflammatory response increases the healing time of the incision, and increases the probability that one or more pellets may extrude due to external pressures (falling on, sitting on, or bumping the insertion region) or internal pressures (strenuous exercise or muscle contraction).

All of these traumatic trocar insertion concerns are amplified particularly for male testosterone replacement therapy, which requires large gauge trocars and high quantities of implanted pellets. The large trocar gauge and high dosage causes a corresponding amount of pain, scarring, and risk of pellet extrusion.

Therefore, it would be beneficial to provide an apparatus, system, and method of subcutaneous pellet delivery that causes little or no trauma to the subcutaneous tissue.

SUMMARY

An atraumatic trocar apparatus, system, kit, and method of use are described. The atraumatic trocar apparatus includes a cannula and an obturator. The cannula includes a tubular cannula body, a medication slot, a posterior end, and an anterior end with a surface that includes a smooth edge. The posterior end of the tubular cannula body includes a first coupling element. The obturator includes an anterior rounded tip, a tubular obturator body, at least one opening proximate to the anterior rounded tip of the obturator, and a second coupling element.

The obturator and cannula assemble to form the atraumatic trocar apparatus when the obturator extends through the tubular cannula body so that the anterior rounded tip of the obturator the at least one opening proximate to the anterior rounded tip of the obturator, and an anterior portion of the tubular obturator body extend past the anterior end of the tubular cannula body when the first coupling element and the second coupling element are coupled to one another. The obturator is configured to create a fluid channel within a subcutaneous tissue by delivering a hydrodissecting fluid solution through the at least one opening proximate to the anterior rounded tip.

An atraumatic subcutaneous medication kit for delivering a medication is also described. The atraumatic subcutaneous medication kit includes a cannula, an obturator, and an outer package. The outer package includes the cannula and the obturator.

In another embodiment, the cannula includes a cannula handle fixedly coupled to the cannula. Additionally, the obturator includes a handle fixedly coupled to the obturator.

The method for atraumatic subcutaneous medication delivery includes inserting an assembled atraumatic trocar through an incision. The assembled atraumatic trocar is inserted into a subcutaneous tissue. The atraumatic trocar includes a cannula and an obturator. The cannula includes a tubular cannula body having an anterior end, a posterior end, and a medication slot disposed along the tubular cannula body. The obturator includes an anterior rounded tip and a tubular obturator body.

The obturator is passed through the tubular cannula body so that the anterior rounded tip of the obturator extends past the anterior end of the tubular cannula body to form the assembled atraumatic trocar. The assembled atraumatic trocar is then used to probe the incision into the subcutaneous tissue along an insertion path within the subcutaneous tissue up to an insertion length. Upon reaching this insertion length, the obturator is removed from the tubular cannula body and two or more medication pellets are placed in the medication slot. The tubular cannula body having the two or more medication pellets placed therein receives the obturator and the obturator anterior rounded tip is used to pass the two or more medication pellets through the tubular cannula body. The obturator pushes the two or more medication pellets so that they exit the anterior opening of the tubular cannula body and enter the delivery site. A first medication pellet and a second medication pellet of the two or more medication pellets are aligned along a non-linear delivery path between the delivery site and the incision.

FIGURES

The presently disclosed subject matter will be more fully understood by reference to the following drawings which are presented for illustrative, not limiting, purposes.

FIG. 3A shows an end-on view of an illustrative insertion obturator rounded tip with seven (7) openings.

FIG. 3B shows an end-on view of an illustrative insertion obturator rounded tip with five (5) openings.

FIG. 3C shows a perspective view of an insertion obturator rounded tip with openings proximate to the end of the tip.

FIG. 7A shows a side view of an illustrative punch scalpel.

FIG. 7B shows an end-on view of the illustrative punch scalpel.

FIG. 7C shows a bottom view of the illustrative punch scalpel.

FIG. 9A shows a side view of the illustrative cannula loaded with medication pellets and the delivery obturator immediately prior to displacement and delivery of the medication pellets.

FIG. 9B shows a side view of the illustrative cannula loaded with medication pellets and the delivery obturator inserted into the cannula and pushing the medication pellets into one another and up to an anterior opening of the cannula.

FIG. 9C shows a side view of the illustrative cannula loaded with medication pellets and the delivery obturator inserted into the cannula and pushing the medication pellets into one another so that a first medication pellet is displaced.

FIG. 9D shows a side view of the illustrative delivery obturator fully inserted into the cannula and the pellets fully displaced and delivered as disclosed herein.

Figure 14A:
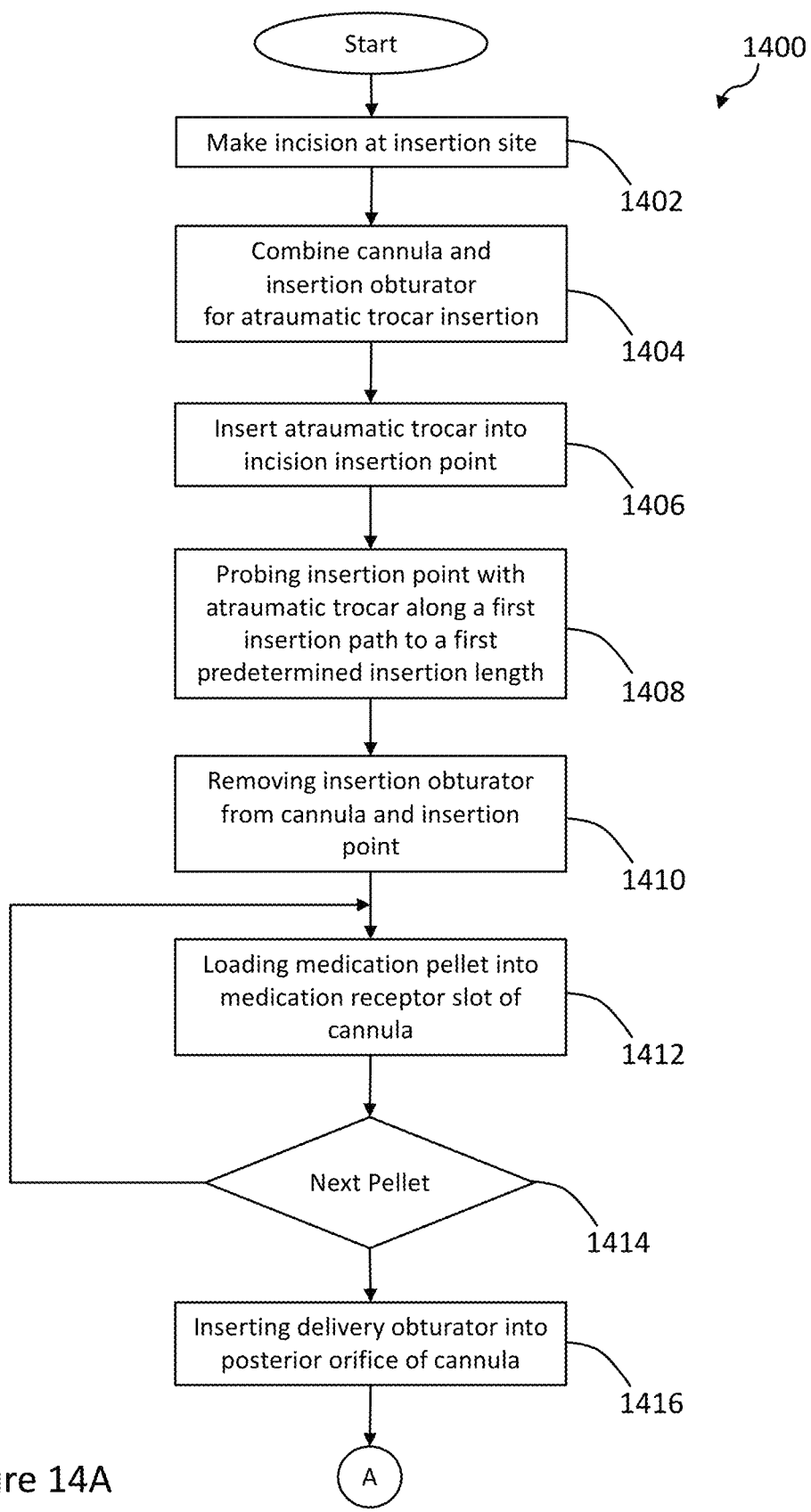
Figure 14B:
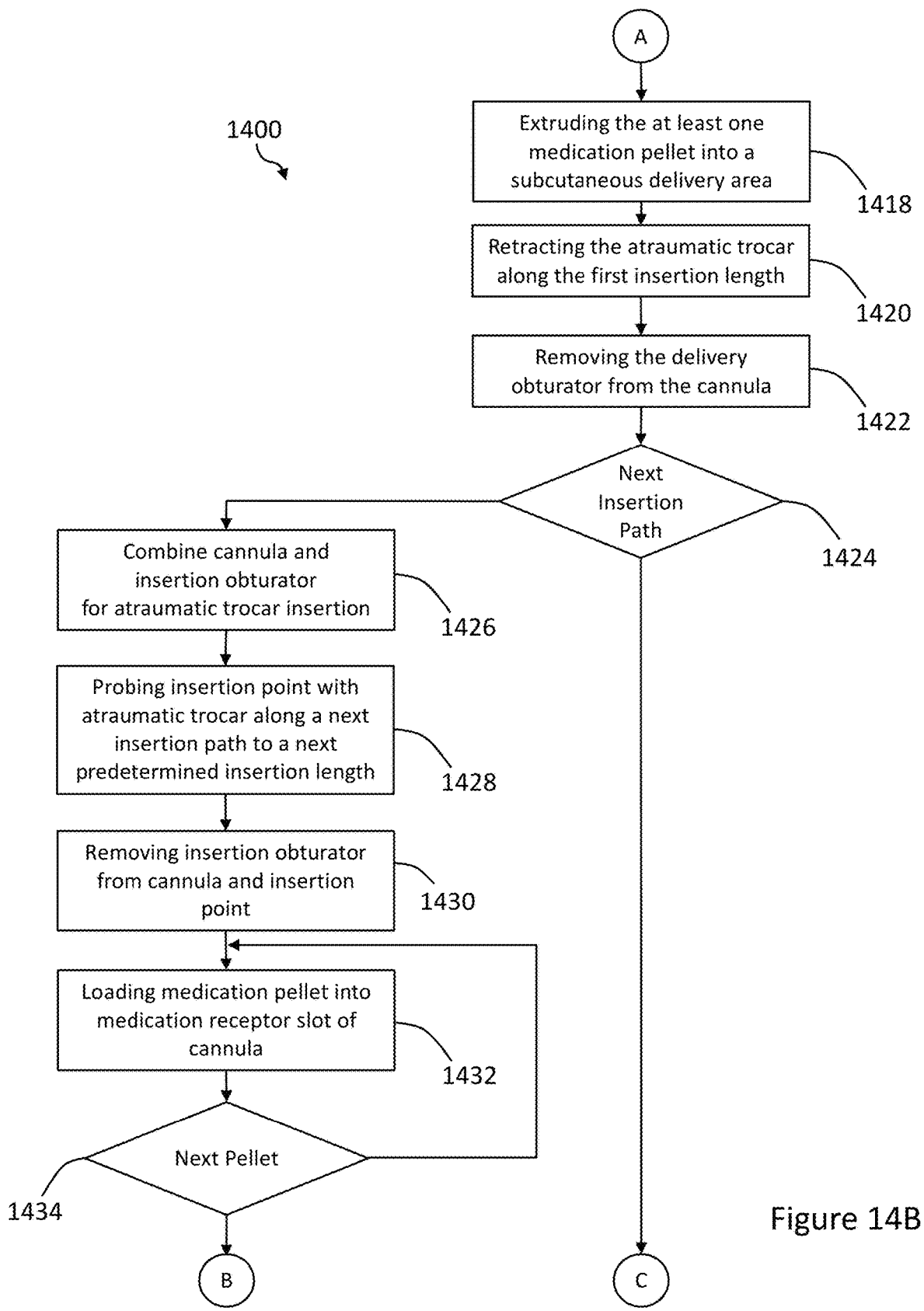
Figure 14C:
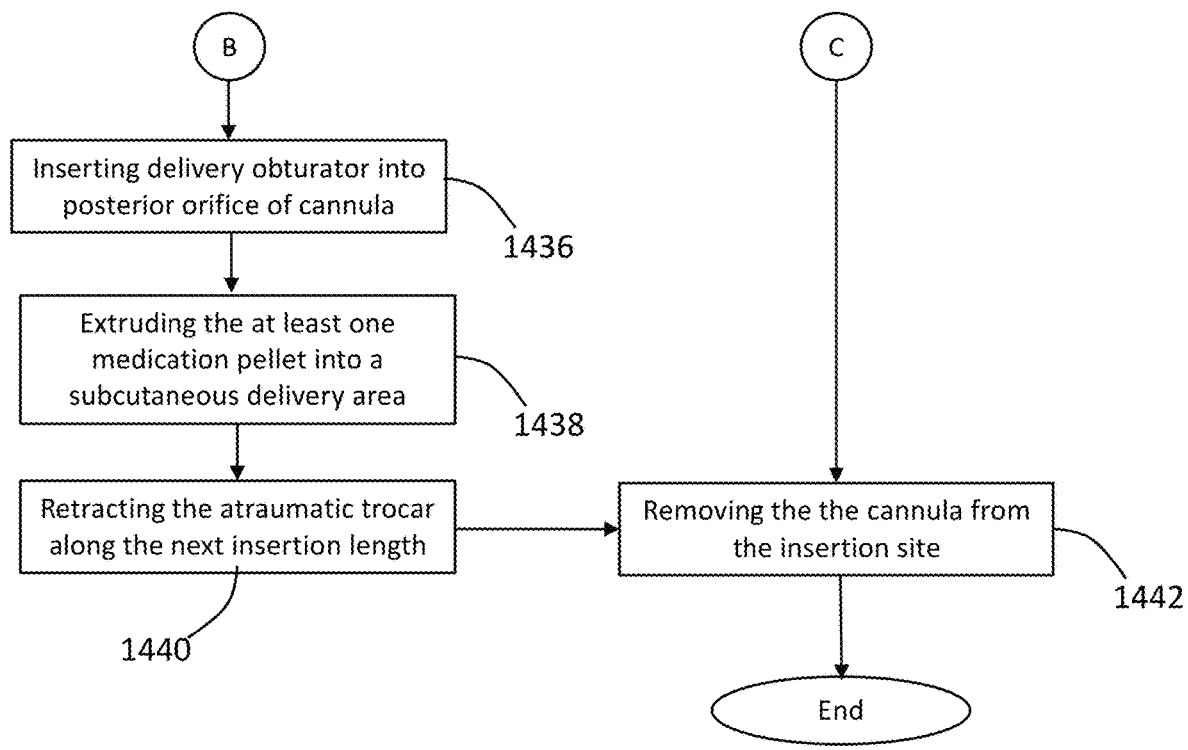

FIGS. 14A, 14B, and 14C show an illustrative atraumatic subcutaneous pellet insertion method.

Figure 15:
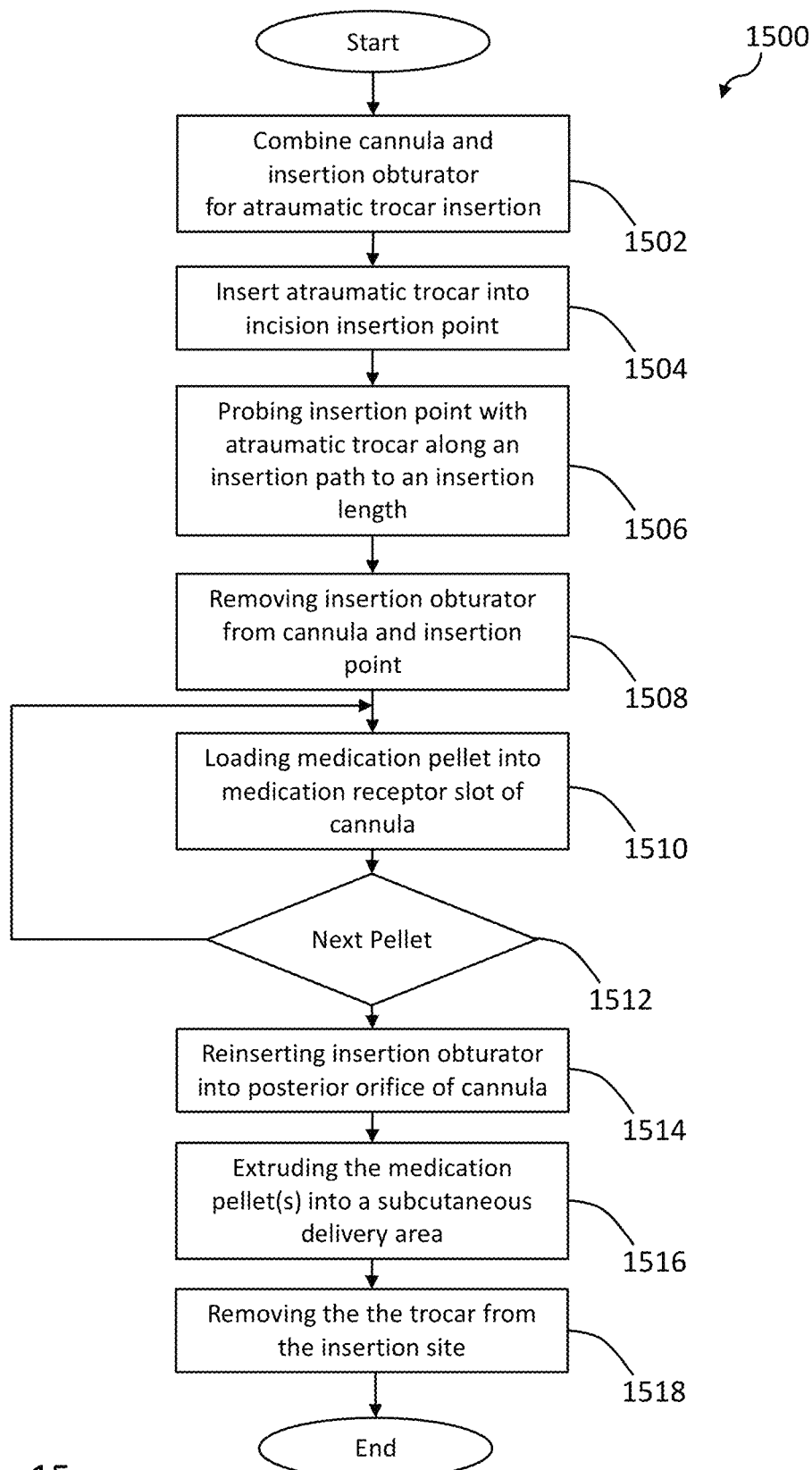

FIG. 15 shows a second illustrative atraumatic subcutaneous pellet insertion method.

Figure 16A:
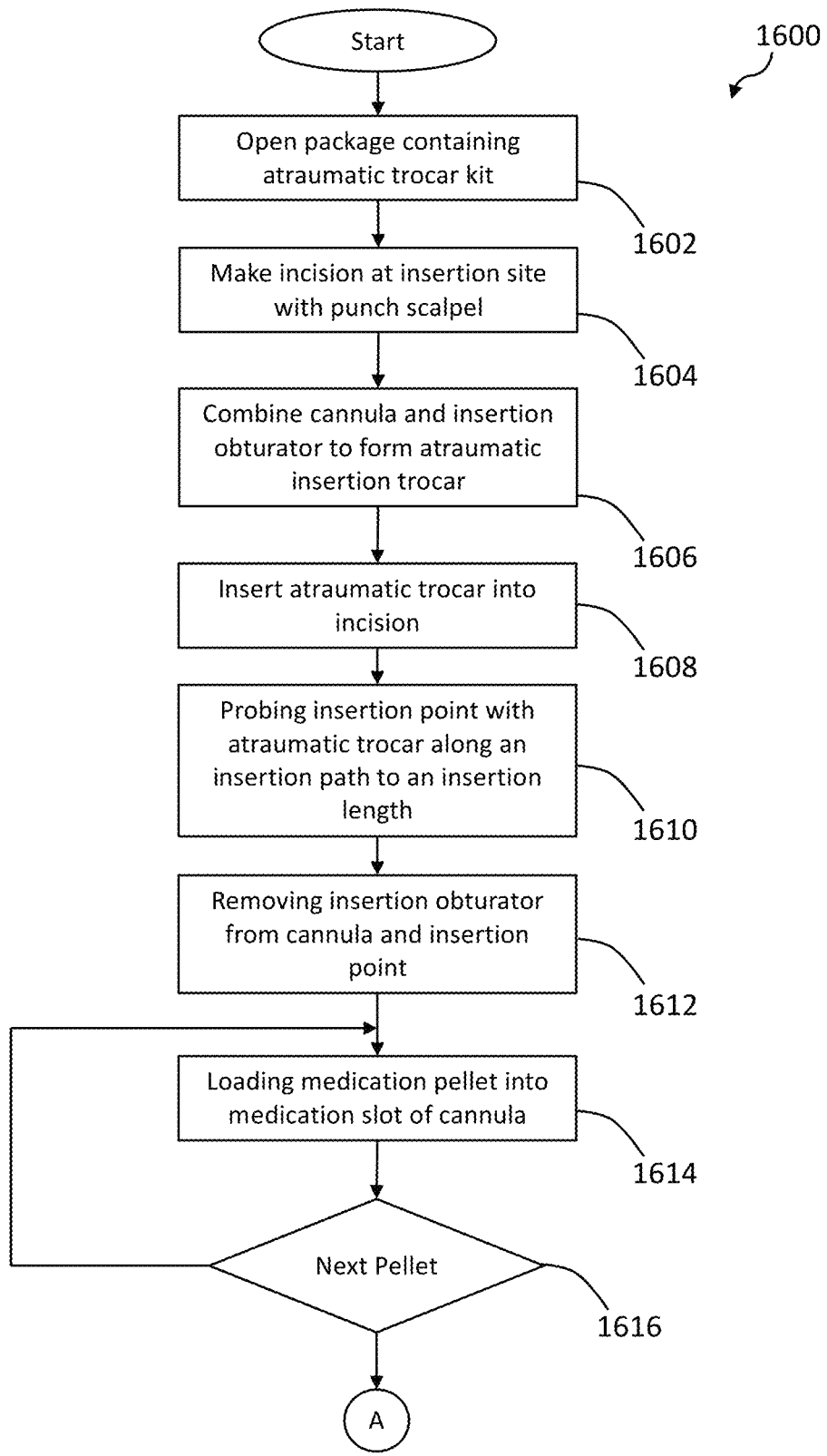
Figure 16B:
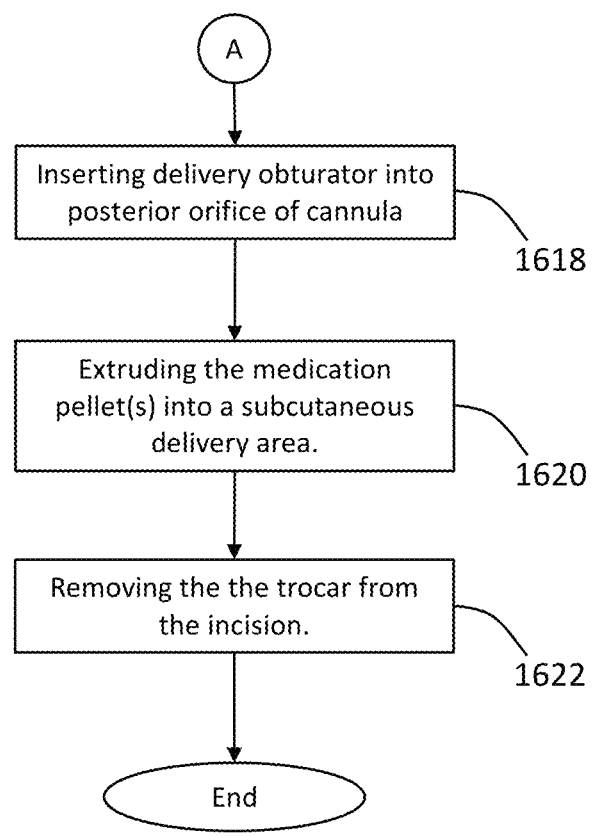

FIGS. 16A and 16B show an illustrative method of using a disposable trocar kit to atraumatically insert medication pellets into subcutaneous tissue.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and methods described herein may vary as to configuration and as to details. The following detailed description of the illustrative embodiments includes reference to the accompanying drawings, which form a part of this application. The drawings show, by way of illustration, specific embodiments in which the invention may be practiced. It is to be understood that other embodiments may be utilized and structural changes may be made without departing from the scope of the claims.

The apparatus, systems and methods described herein are used to insert an illustrative medication pellet into subcutaneous tissue. Medication pellets may be used for hormone replacement and for other applications that would require a relatively slow and sustained release of one or more medications. Thus, a single pellet may be compounded to contain multiple medications, or different medications may be compounded into individual pellets and delivered together as separate pellets at one insertion site. Pellets inserted atraumatically release medication at consistent and measurable rates for several months up to a year or more. Atraumatic implantation therefore, requires fewer visits to a doctor's office during a course of treatment compared to injections (lasting for only a matter of days), and provides more consistent dosages than patches, creams, and pills. This makes atraumatically inserted implants or pellets more efficacious than patches, creams, and pills, and more cost effective than injections requiring frequent trips to a doctor's office.

Atraumatic subcutaneous medication insertion is also viable for treating pain. Chronic pain management techniques include subdermal surgical insertion of a reservoir and/or pump connected to a catheter that runs directly to the patient's spine to deliver morphine or other anesthetics. This technique may afford relief to a patient for several months between doctor's visits, however the system costs tens of thousands of dollars. In contrast, the atraumatic trocar apparatus, system, and method disclosed herein is much more affordable, even allowing for single-use disposable embodiments that delivery relief for several months as well.

As used herein, the term "medication" or "medicinal" includes, but is not limited to, hormones, hormone therapy, pain medication, addiction therapy, and other such drugs. More specifically, the term "medication" may be used to refer to drugs such as testosterone, estradiol (estrogen), fentanyl, morphine, various opiates, naltrexone, lidocaine and other such drugs. By way of example and not of limitation, "medication" may refer to hormones, opioids, numbing agents, and competitive antagonists in metabolic pathways. For example, "medication" may refer to medicine in pellet form that blocks receptors in the brain, which aid in the treatment of addictive disorders including, but not limited to, alcohol and narcotics.

Atraumatic pellet insertion corresponding to the apparatus, systems, and methods disclosed herein can be used for various regimens that include hormone therapy, pain management, and addiction treatment. Further, the apparatus, systems, and methods disclosed herein can be employed in veterinary treatments as well.

With respect to hormone therapy, synthetic, bioidentical, or natural hormones may be used to supplement endogenous hormones naturally produced in the human body. The illustrative apparatus, systems, and methods disclosed herein pertain to the use of medication implants or "pellets." The term "pellet" is used generally to describe both medication pellets and/or hormone implants. Pellets may be prescribed medications or custom compounded therapies for symptoms that stem from hormonal imbalances, to manage hormone levels, to block metabolic pathways involved in the processing of alcohol, opioids, and other addictive drugs, and for pain management.

The pellets described herein may be used for hormone therapies such as menopause and low testosterone. During menopause, individuals experience symptoms including hot flashes, sleep disturbances, and night sweats. Sufferers of low testosterone experience chronic fatigue, loss of muscle mass, increased body fat (especially in the waist area), decreased bone mass, mood changes, lower mental capacity, depression, brain fog, and irritability. Testosterone helps regulate heart function, and plays a part in sperm production, bone health, energy levels, concentration, and muscle mass. Most men experience a natural decline in testosterone as they age, creating a large market for testosterone replacement therapy.

As used herein, the term "hormones" may also refer to synthetic hormones, bioidentical hormones and natural hormones. Synthetic hormones frequently do not have the same structure as endogenous hormones. Synthetic hormones may mimic the effects of endogenous hormones on many biological pathways, but they rarely offer the same effectiveness across all biological pathways. Bioidenticals are exact structural replicas of endogenous hormones and are reported to have much lower incidences of side effects as compared to synthetic hormones. Bioidentical hormones may be derived from plants, such as soy or wild yams. Bioidentical hormones are sometimes defined as molecules identical to a hormone produced by the human body. Natural hormones are those produced in nature by various organisms, and similar to bioidenticals, are identical to a hormone produced by the human body.

An atraumatic trocar apparatus, system, and method are described herein. The atraumatic trocar apparatus includes a cannula, an insertion obturator and a delivery obturator. The cannula includes a tubular cannula body having an anterior cannula end with an anterior cannula opening. The cannula also includes a medication slot disposed along a portion of the tubular cannula body. As described herein, the insertion obturator is received by the cannula and passes through the interior passage of the cannula and exits through the anterior cannula opening. The insertion obturator has a rounded anterior tip and one or more openings near the anterior tip, which is configured to deliver numbing agents, anesthetic, and/or hydrodissecting fluid during insertion of the trocar and before insertion of the medication pellets. The delivery obturator is used to deliver the medication pellets to the subcutaneous insertion site.

In other embodiments, the insertion obturator may also be used to deliver medication pellets to the subcutaneous insertion site, eliminating the need for a separate delivery obturator.

The inventor hypothesizes that inserted pellets induce macrophages to aggregate in the injection area through localized angiogenesis. The macrophages then digest the pellet bit by bit from the pellet's outer surface and flush the pellet medication directly into the blood stream over time, resulting in a tissue concentration of the pellet medication corresponding to a desired concentration. Thus, as the pellet size is increased, the medication release period increases, allowing for medication delivery for a period of days up to approximately a year or more. Increasing pellet size also reduces patient cost by reducing the frequency of office visits/operations.

Figure 2A:
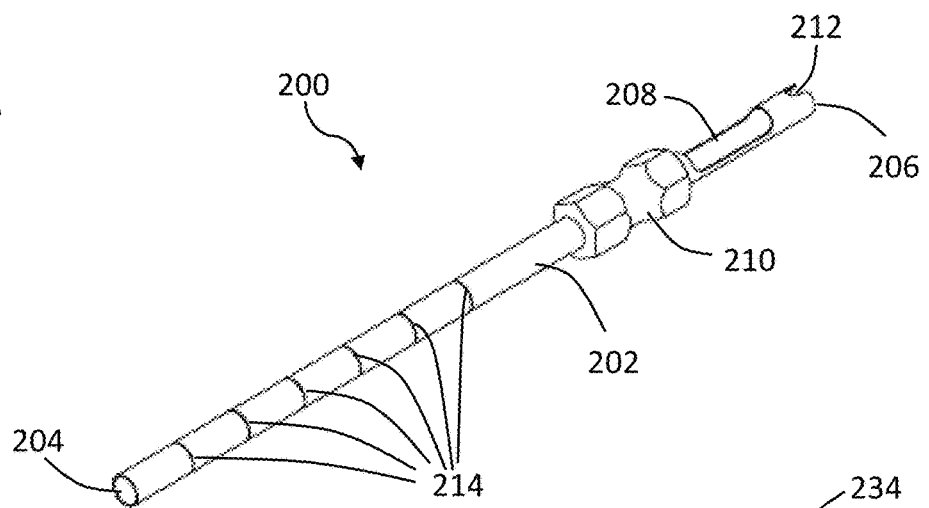
FIG. 2A shows a perspective view of an illustrative embodiment of the cannula as disclosed herein and in accordance with various embodiments.
Figure 2B:
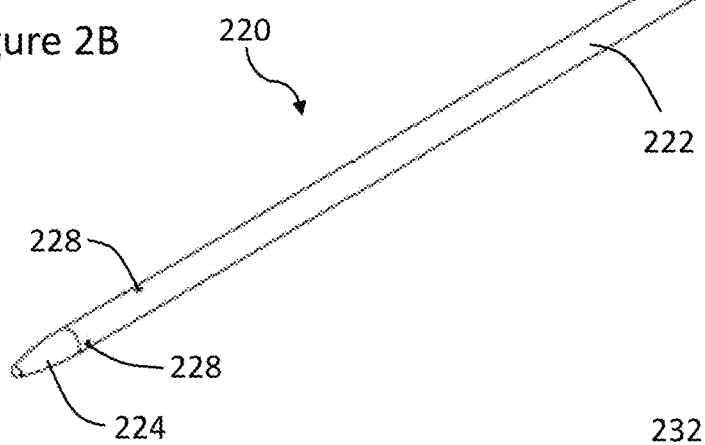
FIG. 2B shows a perspective view of an insertion obturator.
Figure 2C:
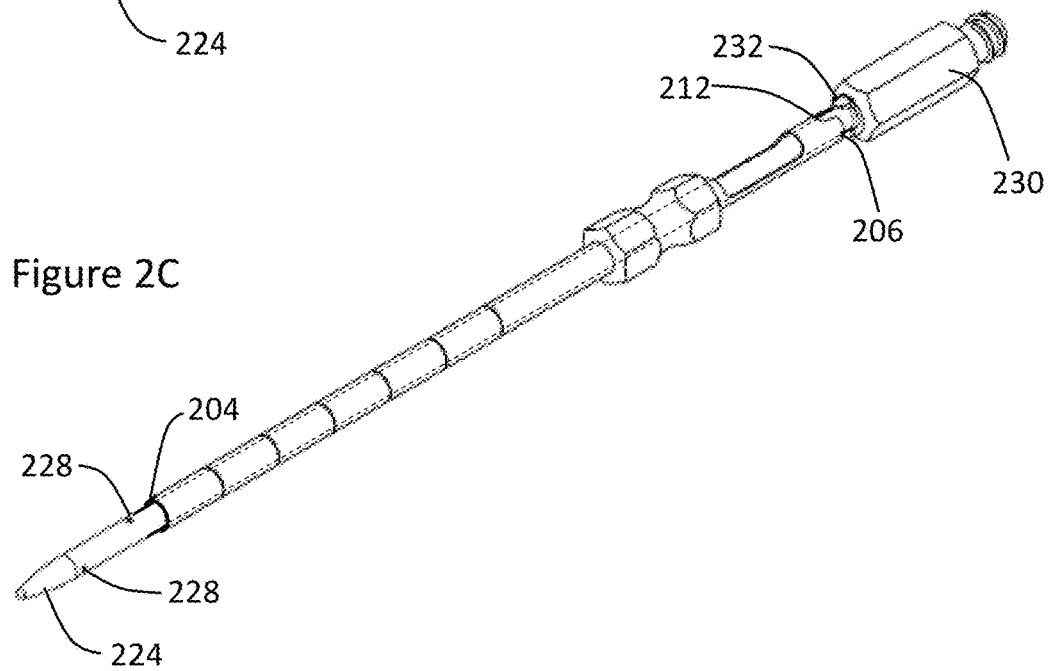
FIG. 2C shows a perspective view of the insertion obturator placed within the interior passage of the cannula.

Referring to FIGS. 2A-C there is shown an illustrative atraumatic trocar apparatus that includes an illustrative cannula and an illustrative insertion obturator. More specifically, FIG. 2A shows an illustrative embodiment of a cannula 200 having a tubular cannula body 202. The tubular cannula body 202 includes an anterior cannula opening 204 located at an anterior end of the cannula 200. The anterior end of the cannula 200 includes a blunt or rounded cylindrical end, which limits the trauma to surrounding tissue during subcutaneous implant procedure. In one embodiment, the cylindrical end of the cannula is blunted by beveling the end. This blunting may also be achieved with a chamfer, a fillet, rounding to create a rounded shape, or any other method of smoothing the right angle where the outer surface of the tubular body of the cannula meets the cylindrical end of the cannula. In another embodiment, the cylindrical end of the cannula is blunted by burnishing the end. The tubular cannula body 202 further includes a posterior cannula opening 206 located at a posterior end of the cannula 200. The tubular cannula body 202 is hollow, providing a passage through the cannula 200 and connecting the anterior cannula opening 204 to the posterior cannula opening 206. Thus, the tubular cannula body 202 includes an interior passage disposed between the posterior cannula end 206 and the anterior cannula end 204. In various embodiments, the anterior blunt surface surrounds the anterior cannula opening.

In the illustrative embodiment, the cannula 200 further includes a slot 208 on a portion of the tubular cannula body 202. The slot 208 is configured or sized to receive a medication pellet and thereby allow the medication access to the interior passage of the cannula 200. The slot 208 may be located proximate to the anterior cannula end. In an alternative embodiment, the cannula 200 may not include a slot on the tubular cannula body 202, instead receiving medication pellets at the posterior end of the cannula.

By way of example and not of limitation, the illustrative medication pellets described in the embodiments presented herein may include male 200 mg testosterone pellets that have a 13 mm length and 4 mm diameter, or male 250 mg testosterone pellet that is 5.6 mm in diameter. Additionally, an illustrative female 87.5 mg testosterone pellet has a 10 mm length and 3 mm diameter. Furthermore, the medication pellet may also include estrogen, which is delivered as a tablet having a 3 mm diameter. Thus, in one embodiment, the cannula may be sized for 5.6 mm medication pellets for male hormone replacement therapy, e.g. the interior diameter of the cannula is greater than 5.6 mm. In another embodiment, the cannula may be sized for 4 mm medication pellets for male hormone replacement therapy, e.g. the interior diameter of the cannula is greater than and less than 5.6 mm. In still another embodiment, the cannula may be sized for 3 mm medication pellets for female hormone replacement therapy, e.g. the interior diameter of the cannula is greater than 3 mm and less than 4 mm.

The illustrative cannula 200 may further include a cannula handle 210 fixedly coupled to the tubular cannula body 202. The cannula handle 210 may be permanently affixed to the exterior of the tubular cannula body 202, such as by welding, or removably affixed to the tubular cannula body 202, such as by threading or chemical means. Further, the tubular cannula body 202 and the cannula handle 210 may be machined from a single piece.

By way of example and not of limitation, each of the components of the atraumatic trocar apparatus, system and kit may be formed from metallic compounds, metal alloys, plastic materials, polymers or other such materials. The material selected for the atraumatic trocar may depend upon whether the atraumatic trocar is disposable or reusable. For example, a reusable atraumatic trocar apparatus may be constructed from stainless steel so that it can be disinfected in an autoclave. While a disposable atraumatic trocar may be composed of a plastic material that is intended for single use and disposal.

The illustrative cannula 200 may further include an illustrative notch 212 located at the posterior end of the tubular cannula body 202. In the illustrative embodiment, the notch 212 is triangular in shape and configured to interface with a tab on an obturator inserted into the interior passage of the cannula 200, as described below. In a further embodiment, the illustrative cannula 200 may include a second notch (not shown) in a second position at the posterior end of the tubular cannula body 202.

The illustrative cannula 200 may further include one or more cannula markings 214 along the tubular cannula body 202. In various embodiments, the cannula markings 214 are visible on the exterior of the tubular cannula body 202. Visibility of the cannula markings 214 may be achieved by scoring, embossing, raising, or coloring. Coloring may include paint, ink, anodizing, or other similarly permanent and visible techniques suitable for use in sterile operations. Where the cannula markings 214 are not scored, embossed, or raised, the cannula markings 214 may be flush with the exterior of the tubular cannula body 202. The cannula markings 214 correspond to a medication length, and serve to aid a doctor or assistant in determining the number of medications or amount of medications administered through the cannula 200. In the illustrative embodiment, the markings 214 are laser etched onto the surface of the cannula 200. In another embodiment, the cannula 200 may include only a single marking 214.

By way of example and not of limitation, the cannula markings 214 may be scored on the surface of an illustrative stainless steel cannula. Alternatively, for a plastic cannula, the cannula markings may be embodied as raised bars, sunk depressions, or flush colored sections on the exterior of the cannula body.

More generally, the illustrative cannula 200 has a length that may range from thirteen (13) centimeters up to seventeen (17) centimeters. The cannula length is measured from the anterior cannula opening 204 to the posterior cannula opening 206. More specifically and by way of example and not of limitation, the illustrative tubular cannula body is composed of stainless steel and has an outer diameter 0.219 inches and an inner diameter of 0.199 inches; thus, the wall thickness of the tubular cannula body is 0.010 inches. Additionally, the illustrative tubular cannula body has a length of 6.07 inches.

In various embodiments, the cannula outer diameter may range from 0.1 inches up to 0.25 inches; the cannula inner diameter may range from 0.08 inches up to 0.23 inches. While the wall thickness of the tubular cannula body may range from 0.005 inches up to 0.05 inches.

Referring now to FIG. 2B, there is shown an illustrative embodiment of an insertion obturator 220 having a tubular insertion obturator body 222, an anterior rounded tip 224, and a posterior insertion obturator opening 226. The tubular insertion obturator body 222 is hollow from the anterior rounded tip 224 to and through the posterior insertion obturator opening 226. By way of example and not of limitation, the illustrative insertion obturator has a length of 7.5 inches, an outer diameter of 0.188 inches and an inner diameter 0.168 inches; thus, the wall thickness for insertion obturator is 0.010 inches.

In various embodiments, the insertion obturator outer diameter may range from 0.07 inches up to 0.225 inches; the insertion obturator inner diameter may range from 0.02 inches up to 0.21 inches. While the wall thickness of the tubular insertion obturator body may range from 0.005 inches up to 0.05 inches.

The illustrative insertion obturator 220 further includes one or more openings 228 located along the tubular insertion obturator body 222. The openings 228 form a passage from the exterior of the tubular insertion obturator body 222 to the interior of the tubular insertion obturator body 222. In the illustrative embodiment, the openings 228 are arranged on the insertion obturator 220 from the anterior rounded tip 224 along the entire length of the insertion obturator body 222 in a spiral orientation. In other embodiments, the openings 228 may be located on and about the anterior rounded tip 224. By way of example and not of limitation, the openings are approximately 0.040 inches in diameter. In various embodiments, the openings can range in diameter from 0.01 inches up to 0.1 inches.

The openings 228 enable the obturator to more easily separate the subcutaneous tissue, adipose tissue, blood vessels, and nerves through hydrodissection. Hydrodissection is a well known technique in ophthalmologic surgery and general surgery where a fluid, such as saline is injected into a target tissue to create a previously non-existent surgical plane. In ophthalmologic surgery hydrodissection is used to create space within the lens, thereby improving a surgeon's ability to perform maneuvers during extracapsular or phacoemulsification surgeries. In general surgery hydrodissection is used in conjunction with ultrasonic guidance to treat peripheral nerve entrapments by releasing the nerves' adhesions from neighboring structures. When releasing entrapped nerves with hydrodissection the fluid used may be platelet-rich plasma ("PRP") or a 5% dextrose solution ("D5W"). In the illustrative embodiments disclosed herein the hydrodissecting fluid delivered through the openings 228 includes PRP, D5W, saline, anesthetic, a numbing solution, or any combination thereof. Hydrodissection during the atraumatic subcutaneous pellets delivery systems and methods disclosed herein allows the obturator to separate the subcutaneous tissue, adipose tissue, blood vessels, and nerves immediately prior to arrival of the anterior blunt tip of the insertion obturator. This preparation of the tissue into which the atraumatic trocar is inserted softens and hydrates the tissue, easing and improving the maneuverability of the atraumatic trocar within the tissue.

The illustrative insertion obturator 220 may further include an insertion obturator handle 230 fixedly coupled to the tubular insertion obturator body 222. The insertion obturator handle 230 may be integral to the tubular insertion cannula body 202; permanently affixed to the exterior of the tubular insertion obturator body 222, such as by welding, glue, or epoxy; or removably affixed to the tubular cannula body 202, such as by threading or chemical means.

Further still, the illustrative insertion obturator 220 may include a tab 232 configured to interface with the notch 212 on the posterior end of the cannula 200. The tab 232 may be located adjacent to the insertion obturator handle 230 and may be located on the exterior surface of the insertion obturator tubular body 222. The tab 232 may be raised above the exterior surface of the insertion obturator tubular body 222. The tab 232 is fixedly coupled to one of the insertion obturator handle 230 and the insertion obturator tubular body 222. In various embodiments, the tab 232 and the insertion obturator handle 230 are formed from a single machined piece. In some embodiments, the insertion obturator 220 includes a second tab 233 located at a second position about the exterior surface of the insertion obturator tubular body 222.

In a broad embodiment, the tolerance between the notch 212 and the tab 232 is 0.05 inches. In a narrower embodiment, the tolerance between the notch 212 and the tab 232 is 0.01 inches. In an even narrower embodiment, the tolerance between the notch 212 and the tab 232 is 0.001 inches. And in a still narrower embodiment, the tolerance between the notch 212 and the tab 232 is 0.0005 inches.

The insertion obturator 220 may further include a threaded posterior end 234. The threaded posterior end 234 may be configured to receive a medication, numbing solution, anesthetic, and/or hydrodissecting fluid through a tubing from a syringe pump or other reservoir. By way of example and not of limitation, the threaded posterior end 234 includes a luer lock receptor, which is configured to interface with tubing that delivers a numbing solution, anesthetic, and/or hydrodissecting fluid. The numbing solution may include saline, lidocaine, and/or epinephrine. The tubing can be plastic, rubber, flexible, or rigid. In some embodiments, the threaded posterior end 234 surrounds the posterior insertion obturator opening 226.

More generally, the illustrative insertion obturator 220 has a length that may range from eighteen (18) centimeters up to twenty-two (22) centimeters. The insertion obturator length is measured from the anterior point of the anterior rounded tip 224 to the posterior insertion obturator opening 226.

In various embodiments, the obturator 220 is a single stainless steel or titanium piece, with no weak joints susceptible to failure. Thus, no element of the obturator 220 is likely to break or separate from a main body of the obturator and remain inside a patient's dermis or other cavity.

Referring now to FIG. 2C, there is shown the illustrative insertion obturator 220 inserted into the interior passage of the illustrative cannula 200, in which the portion of the insertion obturator tubular body 222 within the interior passage of the cannula 200 is shown with dotted lines.

In the illustrative embodiment, the insertion obturator 220 is long enough in comparison to the cannula 200, that the rounded tip 224 and at least one opening 228 protrude beyond the anterior end of the cannula 200 and through the anterior cannula opening 204 when the insertion obturator 220 is inserted into the cannula 200 so that the tab 232 interfaces with the notch 212. In this illustrative embodiment, the rounded tip 224 may protrude 1 cm beyond the anterior end of the cannula 200 so that the rounded tip 224 atraumatically separates tissue approximately 1 cm distal or in front of the anterior end of the cannula 200 upon insertion of the assembled trocar into an insertion site or incision site. This additional length of the insertion obturator 220 modifies tissue so that a later inserted medication pellet can be extruded further into the tissue, for example by tunneling the medication pellet through the tissue displaced by the additional length of the insertion obturator 220 extending beyond the anterior end of the cannula 200.

In another embodiment, the insertion obturator 220 is long enough in comparison to the cannula 200, that only the anterior rounded tip 224 protrudes beyond the anterior end of the cannula 200 and through the anterior cannula opening 204 when the insertion obturator 220 is inserted into the cannula 200 so that the tab 232 interfaces with the notch 212.

In other embodiments, the insertion obturator 220 is long enough in comparison to the cannula 200, that the rounded tip 224 and at least one opening 228 protrude beyond the anterior end of the cannula 200 and through the anterior cannula opening 204 when the insertion obturator 220 is inserted into the cannula 200 so that the insertion obturator handle 230 abuts the posterior cannula end.

By way of example and not of limitation, the outer diameter of the insertion obturator is 0.188 inches and the inner diameter of the cannula is 0.199 inches; thus, there is approximately a gap of 0.005 inches between the inner diameter of the cannula and the outer diameter of the insertion obturator.

In various embodiments, the delivery obturator outer diameter may range from 0.07 inches up to 0.225 inches; the delivery obturator inner diameter may range from 0.02 inches up to 0.21 inches. While the wall thickness of the tubular delivery obturator body may range from 0.005 inches up to 0.05 inches.

Thus, in a broad embodiment, the tolerance between the outer diameter of the insertion obturator and the inner diameter of the cannula is 0.05 inches, and the tolerance between the outer diameter of the delivery obturator and the inner diameter of the cannula is 0.05 inches. In a narrower embodiment, the tolerance between the outer diameter of the insertion obturator and the inner diameter of the cannula is 0.01 inches, and the tolerance between the outer diameter of the delivery obturator and the inner diameter of the cannula is 0.01 inches. In an even narrower embodiment, the tolerance between the outer diameter of the insertion obturator and the inner diameter of the cannula is 0.001 inches, and the tolerance between the outer diameter of the delivery obturator and the inner diameter of the cannula is 0.001 inches. And in a still narrower embodiment, the tolerance between the outer diameter of the insertion obturator and the inner diameter of the cannula is 0.0005 inches, and the tolerance between the outer diameter of the delivery obturator and the inner diameter of the cannula is 0.0005 inches.

Referring now to FIG. 3A, there is shown an illustrative insertion obturator anterior rounded tip 223 and seven (7) openings 228. The illustrative openings 228 may be proximate to the anterior rounded tip 224 and are arrayed in a spiral pattern along the tubular body of the insertion obturator 222, such that a second opening is 1 cm further from the anterior rounded tip 223 than a first opening and radially separated from the first opening by an angle of 30 degrees. This separation may be greater, such as 2 cm and 60 degrees, or any combination of these linear and radial separations. Generally, the spiral pattern is achieved by continuation the same separation from the second opening to a third opening as that from the first opening to the second opening. The openings 228 pass through the outer surface of the insertion obturator to the interior. In an alternative embodiment, the openings 228 are arrayed in a plane perpendicular to the length of the insertion obturator 220, and located in proximity to the anterior rounded tip 224, such as within 2 cm of the anterior rounded tip 224. In a modification of this alternative embodiment, the openings 228 are arrayed in a plane perpendicular to the length of the insertion obturator 220, and located within 1 cm of the anterior rounded tip 224.

The illustrative insertion obturator 220 may further include one or more delivery markings (not shown) along the tubular body of the insertion obturator 222 for embodiments where the insertion obturator is also used to deliver medication pellets from the cannula 200 to a delivery site. In various embodiments, the delivery markings are visible on the exterior of the tubular body of the insertion obturator 222. Visibility of the delivery markings may be achieved by scoring, embossing, or coloring. Coloring may include paint, ink, anodizing, or any suitable flush marking technique. Where the delivery markings are not recessed or scored, the delivery markings may be flush with the exterior of the tubular body of the insertion obturator 222. The delivery markings correspond to a medication length, and serve to aid a surgeon, nurse, physician's assistant, or other assistant in determining the number of medications or amount of medications administered through the cannula 200 with the insertion obturator 220. In one embodiment, the delivery markings correspond to a medication length of 0.5 inches. In a further embodiment, the delivery markings correspond to cannula markings 214 that are also spaced 0.5 inches apart from one another. However, in alternative embodiments, the delivery markings and cannula markings 214 correspond to medication lengths ranging from 0.1 inches to 0.7 inches.

Referring now to FIG. 3B, there is shown another illustrative insertion obturator anterior rounded tip 225 and five (5) openings 228. The illustrative openings 228 may be proximate to the anterior rounded tip 225 and are arrayed in a spiral pattern along the tubular body of the insertion obturator 222. The openings 228 pass through the outer surface of the insertion obturator to the interior.

Referring now to FIG. 3C, there is shown a side view of an illustrative insertion obturator anterior rounded tip 227 and seven (7) openings 228 arrayed in a plane perpendicular to the length of the insertion obturator. Three (3) of the openings 228 are in view, one (1) opening 229 is partially in view, and the remaining three (3) openings are not visible on the reverse side of the insertion obturator.

As the number of openings proximate to the delivery obturator tip 224 increase, the strength and durability of the tip 224 decrease. Therefore, certain embodiments may include fewer openings, such as one or two openings. The reduced number of openings increases the structural integrity of the insertion obturator 220, and in particular the anterior rounded tip 224 of the insertion obturator 220. A further attribute of reducing the number of openings is an increased pressure of numbing solution or anesthetic delivered through the opening(s). As described below, increasing the delivery pressure of the numbing solution may achieve hydrodissection, which has the advantageous effect of softening tissues and creating a surgical plane or fluid channel into which pellets are delivered.

Figure 4A:
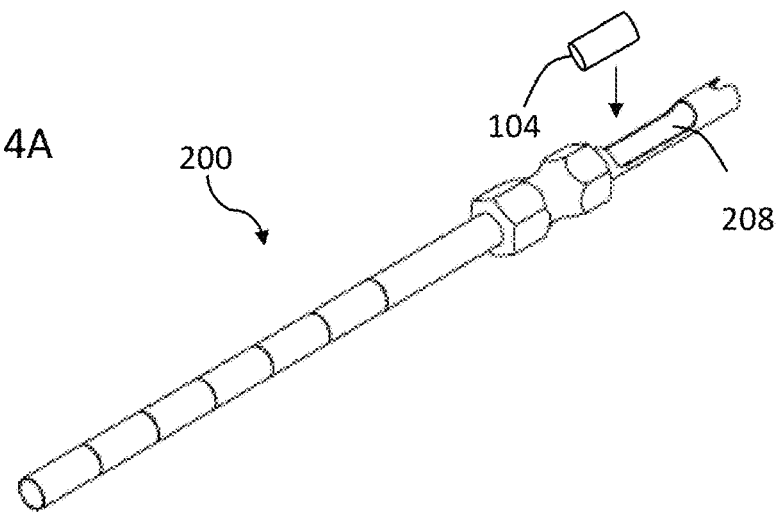
FIG. 4A shows a perspective view of the cannula receiving a medication pellet.

With reference now to FIG. 4A, there is shown an illustrative cannula 200 receiving a medication pellet 104 at the medication slot 208. The received medication pellet resides within the interior passage of the cannula 200. By way of example and not of limitation, the medication slot 208 is 0.56 inches long and is configured to receive a 0.5 inch long medication pellet 104.

Figure 4B:
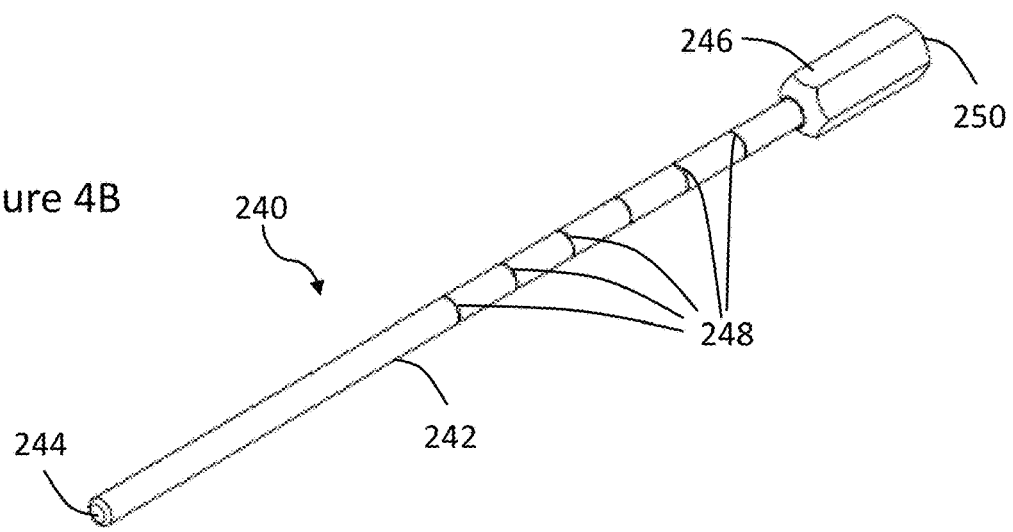
FIG. 4B shows a perspective view of a delivery obturator.

Referring now to FIG. 4B, there is shown an illustrative delivery obturator 240 having a cylindrical shaft 242 and an anterior blunt tip 244. The illustrative delivery obturator 240 may further include a delivery obturator handle 246 affixed to the cylindrical shaft 242.

In the illustrative embodiment, the anterior cannula end is blunt and in combination with the blunt tip of the delivery obturator 240 forms a blunt surface. The blunt surface formed by the anterior cannula end and anterior blunt tip of the delivery obturator 240 may be a continuous smooth surface or a semi-continuous smooth surface. A similarly continuously smooth or semi-continuously smooth blunt surface or edge may be formed by the blunt anterior cannula end and the anterior blunt tip of the insertion obturator. In the illustrative embodiment, the blunt surface includes rounded or beveled edges of the anterior end of the cylindrical shaft 242. The combination of the anterior cannula end and the blunt tip 244 of the delivery obturator 240 is blunt or rounded to reduce or prevent instances of tissue tearing during the subcutaneous pellet insertion procedure.

In the illustrative embodiment, the delivery obturator handle 246 is located at a posterior end of the delivery obturator 240. The illustrative delivery obturator 240 may further include one or more delivery markings 248 along the cylindrical shaft 242. In various embodiments, the delivery markings 248 are visible on the exterior of the cylindrical shaft 242. Visibility of the delivery markings 248 may be achieved by scoring, embossing, or coloring. Coloring may include paint, ink, anodizing, or any suitable flush marking technique. Where the delivery markings 248 are not recessed or scored, the delivery markings 248 may be flush with the exterior of the cylindrical shaft 242. The delivery markings 248 correspond to a medication length, and serve to aid a surgeon, nurse, physician's assistant, or other assistant in determining the number of medications or amount of medications administered through the cannula 200 with the delivery obturator 240. In one embodiment, the delivery markings 248 correspond to a medication length of 0.5 inches. In a further embodiment, the delivery markings 248 correspond to cannula markings 214 that are also spaced 0.5 inches apart from one another. However, in alternative embodiments, the delivery markings 248 and cannula markings 214 correspond to medication lengths ranging from 0.1 inches to 0.7 inches. In further embodiments, the insertion obturator 220 bears the delivery markings corresponding to a medication length and the cannula markings 214.

More generally, the illustrative delivery obturator 240 has a length that may range from sixteen (16) centimeters up to twenty (20) centimeters. The delivery obturator length is measured from the anterior blunt tip 244 to a posterior end 250 of the delivery obturator 240.

Figure 4C:
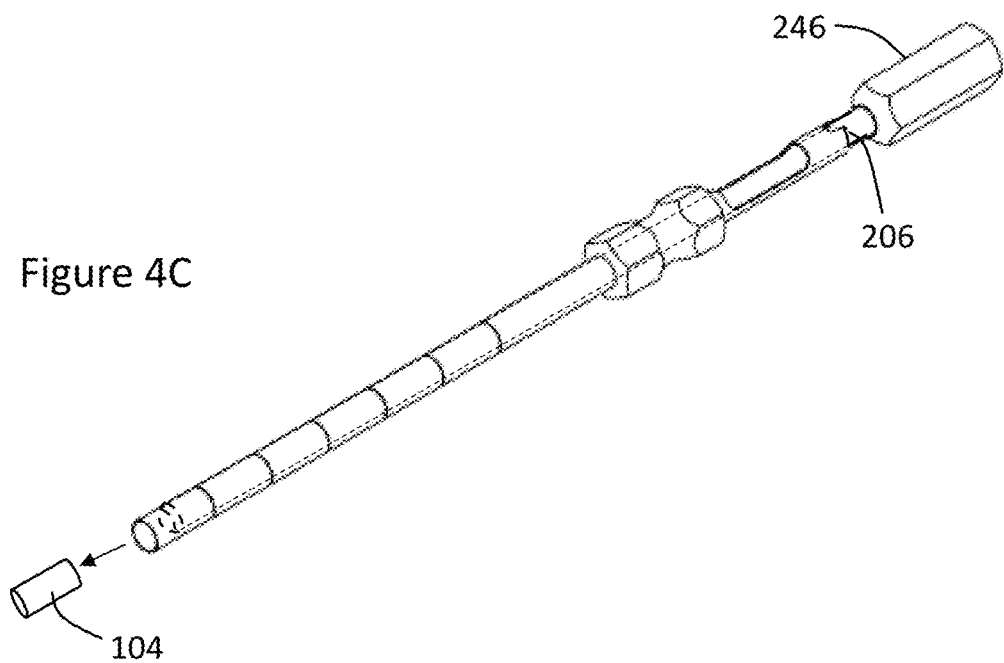
FIG. 4C shows a perspective view of the delivery obturator placed within the interior passage of the cannula so that the delivery obturator delivers a medication pellet.

Referring now to FIG. 4C, there is shown the illustrative delivery obturator 240 inserted into the interior passage of the illustrative cannula 200 such that at least one medication pellet 104 passes through the anterior opening of the cannula 200. The portion of the delivery obturator cylindrical shaft 242 within the interior passage of the cannula 200 is shown with dotted lines. The delivery obturator 240 is long enough in comparison to the cannula 200 that the anterior blunt tip 244 is of sufficient length to pass the medication pellet(s) through the cannula.

For example, the delivery obturator 240 may extend to within one (1) centimeter of the anterior end of the cannula 200. In this embodiment, the delivery obturator is long enough to push at least one pellet 104 to the anterior cannula opening 204, such that a portion of the at least one pellet 104 protrudes through the anterior cannula opening 204.

In an alternative embodiment, the insertion obturator 220 is inserted into the interior passage of the illustrative cannula 200 such that at least one medication pellet 104 passes through the anterior opening of the cannula 200. The insertion obturator 220 is long enough in comparison to the cannula 200 that the anterior blunt tip 244 is of sufficient length to pass the medication pellet(s) through the cannula.

In another embodiment, the delivery obturator 240 is long enough in comparison to the cannula 200 that the anterior blunt tip 244 is flush with the anterior end of the cannula 200 and the anterior cannula opening 204 when the delivery obturator 240 is inserted into the cannula 200 to a maximum allowable extent. The maximum allowable extent is the point at which the delivery obturator handle 246 abuts the posterior cannula opening 206 and the posterior end of the cannula 200.

The atraumatic trocar apparatus described above may be embodied in a kit that includes the cannula 200, the insertion obturator 220, the delivery obturator 240 and an outer package that houses the cannula, insertion obturator and delivery obturator. By way of example and not of limitation, the illustrative atraumatic trocar kit may also include a scalpel, scissors, bandages, antiseptic ointments, and other such materials that may be used during the medical procedure. In another embodiment, the kit includes a cannula and an insertion obturator, but does not include a separate delivery obturator. In still other embodiments, the kit includes a disposable trocar as described below.

Figure 5A:
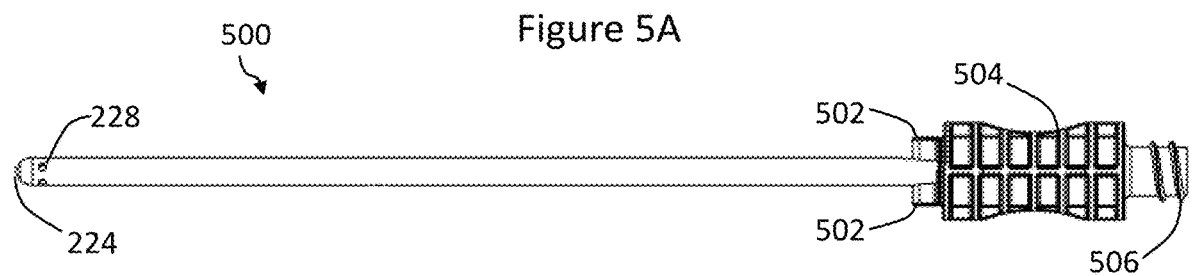
FIG. 5A shows a perspective view of a disposable insertion obturator.

Referring now to FIG. 5A, there is shown an illustrative disposable insertion obturator 500 having five (5) openings 228 arrayed in a plane perpendicular to the length of the disposable insertion obturator 500 proximate to the anterior rounded tip 224. The illustrative disposable insertion obturator 500 also includes two tabs 502, a textured handle 504, and a threaded posterior opening 506. The tabs 502 of the disposable insertion obturator 500 are thicker with respect to the diameter of the insertion obturator tubular body than the embodiments disclosed in FIGS. 2B and 2C because of the structural characteristics of the materials used in the disposable embodiment. For example, plastic used in the disposable embodiments is less resistant to the torsional strain exerted when twisting the textured handle 504 than stainless steel or other metals/metal alloys used in the reusable embodiments.

Figure 5B:
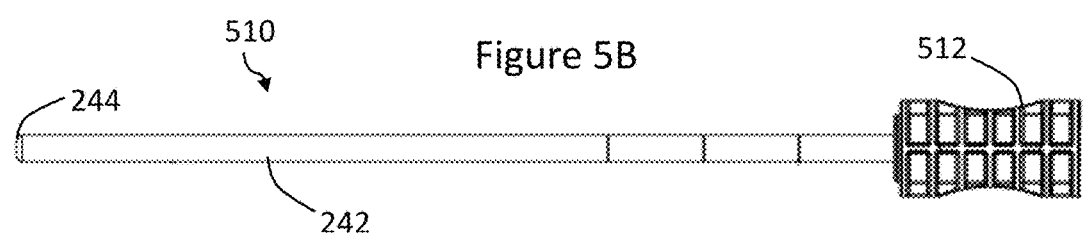
FIG. 5B shows a perspective view of a disposable delivery obturator.

With reference now to FIG. 5B, there is shown an illustrative disposable delivery obturator 510 having a cylindrical shaft 242 and an anterior blunt tip 244. The illustrative disposable delivery obturator 510 further includes a textured handle 512 affixed to the cylindrical shaft 242. In an alternative embodiment, the textured handle 512 is integral to the cylindrical shaft 242.

Figure 5C:
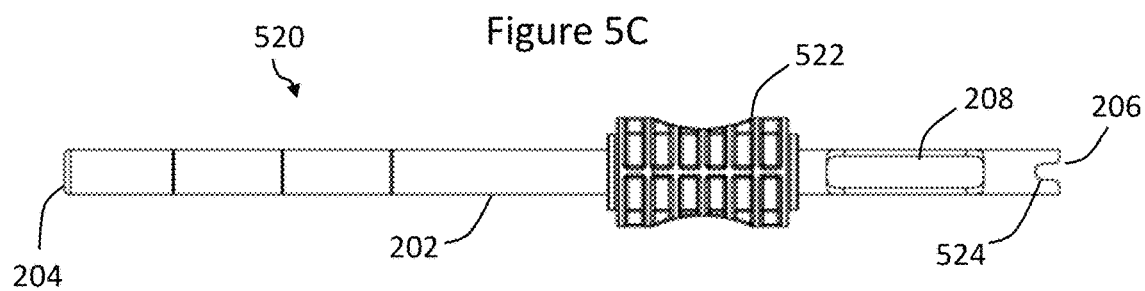
FIG. 5C shows a perspective view of a disposable cannula.

Referring now to FIG. 5C, there is shown an illustrative disposable cannula 520, having a tubular cannula body 202. The tubular cannula body 202 includes an anterior cannula opening 204 located at an anterior end of the disposable cannula 520. The anterior end of the disposable cannula 520 includes a blunt or rounded cylindrical end. The tubular cannula body 202 further includes a posterior cannula opening 206 located at a posterior end of the disposable cannula 520. The tubular cannula body 202 is hollow, providing a passage through the disposable cannula 520 and connecting the anterior cannula opening 204 to the posterior cannula opening 206. Thus, the tubular cannula body 202 includes an interior passage disposed between the posterior cannula end 206 and the anterior cannula end 204.

In the illustrative embodiment, the disposable cannula 520 further includes a slot 208 on a portion of the tubular cannula body 202. The slot 208 is configured or sized to receive a medication pellet and thereby allow the medication access to the interior passage of the disposable cannula 520. The slot 208 may be located anywhere along the disposable cannula 520. However, in the illustrative embodiment, the slot 208 is proximate to the anterior cannula end.

The illustrative disposable cannula 520 may further include a textured handle 522 fixedly coupled to the tubular cannula body 202. The textured handle 522 may be permanently affixed to the exterior of the tubular cannula body 202, removably affixed to the tubular cannula body 202, such as by threading or chemical means, or may be integral to the disposable cannula 520. Thus, the tubular cannula body 202 and the textured handle 210 may be molded as a single piece.

The illustrative disposable cannula 520 may further include two notches 524 located at the posterior end of the disposable cannula 520. In the illustrative embodiment, the notches 524 are shaped and configured to interface with the tabs 502 on the disposable insertion obturator 500 upon full insertion into the interior passage of the disposable cannula 520. In the illustrative embodiment, the notches 524 are arranged on opposites sides of the posterior end of the posterior cannula end, i.e. at 180° intervals. In other embodiments, the disposable cannula includes only one notch 524. In still other embodiments, the disposable cannula includes more than two notches that are arranged to correspond to the position of various tabs 502 on the disposable insertion obturator.

Figure 6:
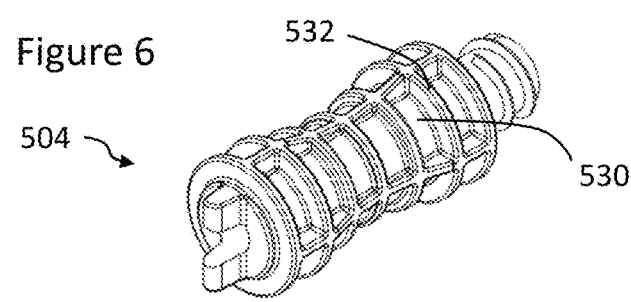
FIG. 6 shows a perspective view of a disposable trocar handle.

Referring now to FIG. 6, there is shown a perspective view of the insertion obturator textured handle 504 in isolation. In the illustrative embodiment, the texture arises from cavities or depressions 530 and ridges 532 on the surface of the textured handle 504.

With reference now to FIGS. 7A-C, there is shown an illustrative punch scalpel 700 that includes a bracket 702 and a scalpel blade 704. Referring now to FIG. 7A, the punch scalpel 700 is shown from the front. The bracket 702 houses the scalpel blade 704 and includes ridges 706 for a texture grip that allows a doctor or other practitioner to more easily grasp the punch scalpel and therefore improves the overall ergonomic design. In some embodiments, the bracket also includes a base 708 that is perpendicular to the scalpel blade 704, and enables a stable placement of the punch scalpel on a patient's dermis. In various embodiments, the punch scalpel 700 can further include a scalpel handle (not shown) extending beyond the scalpel bracket 702 above and connected to the scalpel blade 704. In other embodiments, the bracket base is the same width as the bracket.

With reference now to FIG. 7B, there is shown the illustrative punch scalpel from a side view. In the illustrative example, the ridges 706 are raised above the surface of the bracket 702. However, in various embodiments, the ridges 706 may be depressed below the surface of the bracket 702, or be flush with the surface of the bracket 702 and have a texture that improves or provides a grip. The bracket base 708 extends beyond the thickness of the bracket 702 to create a stable platform for a doctor or other practitioner to brace the punch scalpel against the patient's dermis. The scalpel blade 704 has a thickness that is less than the thickness of the bracket 702, in order to allow the bracket 702 to house the scalpel blade 704.

Referring now to FIG. 7C, there is shown the punch scalpel bracket 702 from below. The punch scalpel bracket 702 includes guide slot 710 that houses the scalpel blade (not shown). Additionally, the base 708 of the bracket 702 includes a guide notch 712 that corresponds to the center of the scalpel blade and the center of any incision made by the scalpel blade.

Figure 8A:
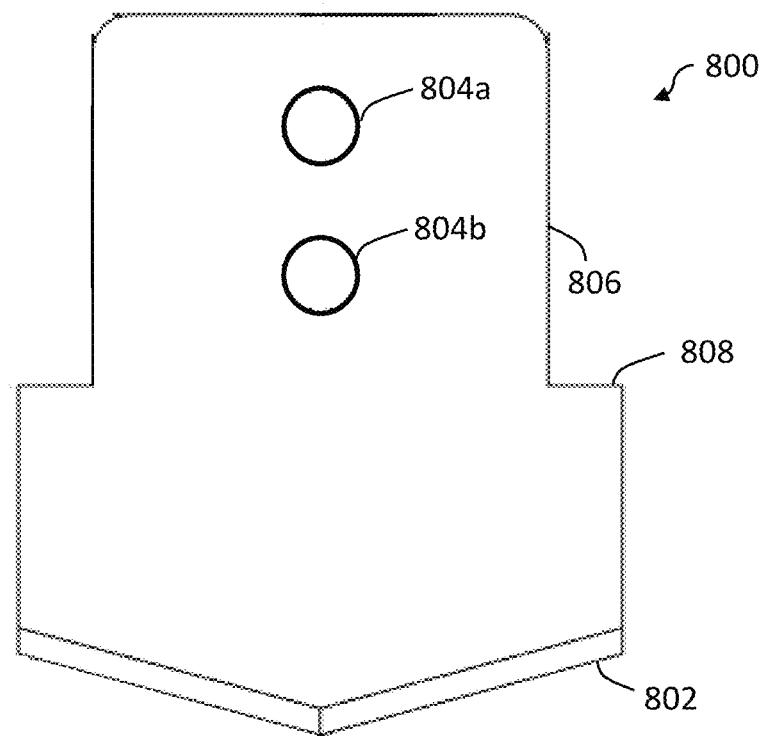
FIG. 8A shows an illustrative punch scalpel blade.
Figure 8B:
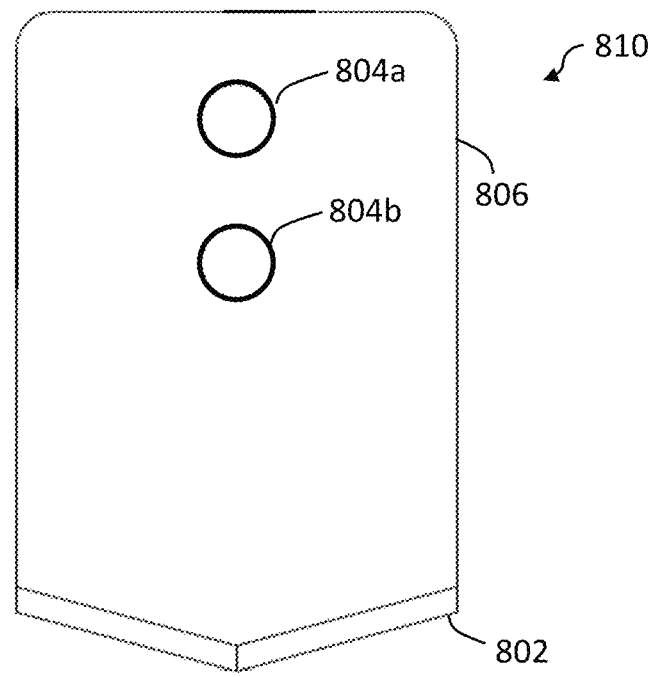
FIG. 8B shows a second illustrative punch scalpel blade.

With reference now to FIGS. 8A and 8B, there is shown illustrative scalpel blades 800 and 810, respectively. Both scalpel blades 800 and 810 include cutting edges 802, as well as mounting points 804a and 804b centered within an upper body 806. Additionally, scalpel blade 800 includes ledge 808, which is an artifact arising from the greater width of the scalpel blade edge 802 with respect to the upper body 806. The mounting points 804a and 804b provide points of attachment for a scalpel handle (not shown) or for guides notches/grooves within the bracket 702.

In one embodiment, the atraumatic trocar kit is a disposable kit that includes the disposable insertion obturator 500, the disposable cannula 520, the punch scalpel 700, and instructions informing a user on how to assemble the disposable trocar and deliver pellets to a subcutaneous delivery site, all housed within a disposable packaging. The disposable packaging can be plastic, paper, rigid, flexible, or any combination thereof. In one embodiment, the package is a tray configured to hold the kit elements and a peel-back covering material that seals with the tray, thereby housing the kit elements. The tray may be plastic, cardboard, or layered paper.

With reference now to FIG. 9A, there is shown an illustrative cannula 200 loaded with several medication pellets 104 and an illustrative delivery obturator 240 positioned near the cannula 200 in preparation to deliver the medication pellets by extruding or forcing the pellets through the cannula 200. As with the earlier description above, the description of this embodiment may employ an insertion obturator instead of the delivery obturator. The length from the most posterior marking 214a on the cannula 200 to the posterior cannula opening 206 and posterior end of the cannula 200 corresponds to the length from the anterior blunt tip 244 to the most anterior marking 248a on the delivery obturator.

Referring now to FIG. 9B, the delivery obturator 240 is inserted into the interior passage of the cannula 200 so that the most anterior marking 248a on the delivery obturator 240 are adjacent to the posterior cannula opening 206. The portion of the delivery obturator 240 that is within the interior passage of the cannula 200 is represented by dotted lines. In this configuration, the blunt tip 244 of the delivery obturator 240 pushes the medication pellets 104 into positions in the interior passage of the cannula 200 corresponding to the cannula markings 214.

Referring now to FIG. 9C, the delivery obturator 240 is inserted into the interior passage of the cannula 200 so that the second most anterior marking 248b on the delivery obturator 240 is adjacent to the posterior cannula opening 206. When the delivery obturator 240 is inserted into the interior passage of the cannula 200 to such a length, the most anterior marking 248a on the delivery obturator 240 is disposed within the interior passage of the cannula 200, the blunt tip 244 of the delivery obturator 240 is aligned with the second most posterior marking 214b of the cannula 200; and the medication pellet 104a passes through the anterior opening 204 of the cannula 200 and delivered.

With reference now to FIG. 9D, the delivery obturator 240 is inserted into the interior passage of the cannula 200 to the full length of the delivery obturator 240, where the delivery obturator handle 246 abuts the posterior opening 206 of the cannula 200. In this configuration, the medication pellets 104 are extruded and delivered even though a portion of the most posterior medication pellet 104b remains within the interior passage of the cannula 200. A portion of the most posterior medication pellet 104b remains within the interior passage of the cannula 200 because this illustrative delivery obturator embodiment has a length that does not extend the blunt tip 244 of the delivery obturator 240 up to or through the anterior opening 204 of the cannula 200 at the anterior end of the cannula 200. The portion of the most posterior medication pellet 104b remaining within the interior passage of the cannula 200 is represented by dotted lines, while the portion of the most posterior medication pellet 104b that has been extruded from or through the anterior opening 204 of the cannula 200 is represented by solid lines. Notably, in embodiments where the delivery obturator is long enough to extend to and/or through the anterior opening of the cannula the most posterior medication pellet 104b is fully ejected from the cannula into the subcutaneous delivery site. This full ejection/extrusion of the most posterior medication pellet 104b also occurs when the insertion obturator is used instead of the delivery obturator because the insertion obturator is long enough to extend through the cannula and out of the anterior cannula opening when inserted into the interior passage of the tubular cannula body.

In other embodiments, the features and methods disclosed by FIGS. 9A-D, may also be performed using an insertion obturator in place of the delivery obturator. Notably, prior art trocar apparatus, systems, and methods required the use of a separate delivery obturator because the angled cutting edge on the insertion obturator was not suitable to delivering pellets. The angled cutting edge could cause the pellet and insertion obturator to become stuck in the cannula or shear/shatter the pellet prior to delivery in subcutaneous tissue. However, the rounded anterior tip of the insertion obturators disclosed herein allow for delivery of pellets to subcutaneous tissue through the cannula without concerns that the pellet will shatter or become stuck.

Figure 10:
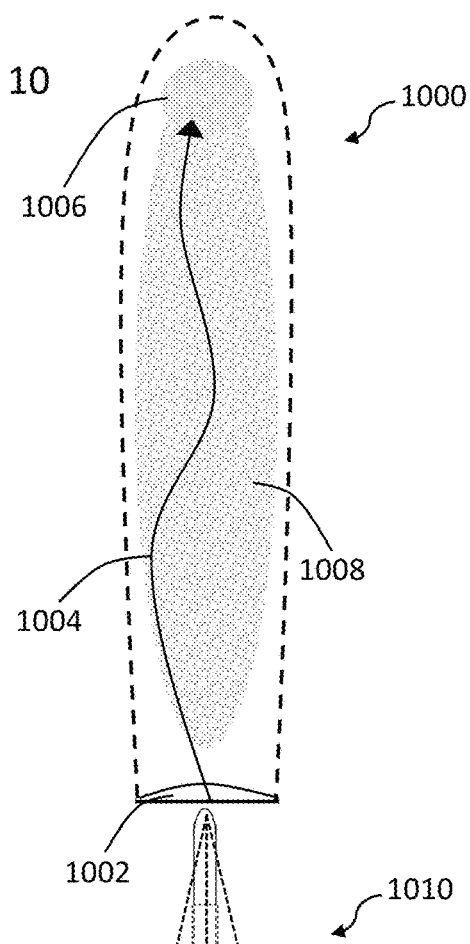
FIG. 10 shows a cut-away view of an illustrative delivery area, assembled insertion trocar, and side-to-side atraumatic subcutaneous probing techniques.

Referring now to FIG. 10, there is shown an illustrative insertion area 1000 and assembled atraumatic insertion trocar 1010 having a centerline 1012. The insertion area 1000 is demarcated by the dotted line representing the boundary of an internal cavity surrounding subcutaneous tissue, and includes an incision site 1002, an insertion path 1004, a delivery site 1006, and a delivery area 1008. The assembled atraumatic insertion trocar 1010 follows the insertion path 1004 to the delivery site 1006 by angling the centerline 1012 along an arc 1014 during insertion from a right centerline extreme 1012a to a left centerline extreme 1012b, repeatedly. The insertion path runs below and approximately parallel to the epidermis tissue layer, through the dermis and ultimately into the subcutaneous tissue, without descending through or below the fascia into muscle skeletal or other tissue/organs.

The precise track of the insertion path 1004 will vary with every insertion depending upon the tissue and other connective structures encountered by the assembled atraumatic insertion trocar 1010. Thus, the back-and-forth weaving of the assembled atraumatic insertion trocar 1010 may oscillate between the right centerline extreme 1012a and the left centerline extreme 1012b inconsistently, such that the oscillating path varies in both frequency and amplitude. For example, a medical professional operating the assembled atraumatic insertion trocar 1010 may direct the assembled atraumatic insertion trocar 1010 from the centerline path 1012 directly between the right centerline extreme 1012a and the left centerline extreme 1012b somewhat towards the right centerline extreme 1012a to bounce off a fibrous septa of tissue, then encounter still more connective or other tissue impeding the progress of the assembled atraumatic insertion trocar 1010 along that path that requires the medical professional direct the assembled atraumatic insertion trocar 1010 further towards the right centerline extreme 1012a before avoiding still another portion of denser tissue (such as peripheral somatic nerves or constricted blood vessels, i.e. arterioles or venuoles) which then causes the medical professional to direct the assembled atraumatic insertion trocar 1010 back towards the left centerline extreme 1012b. In this manner the insertion path 1004 may be irregular and non-linear in order to avoid, slip past, bounce off of, deflect, and prevent trauma or other damage to various tissue structures encountered by the rounded tip.

Figure 11:
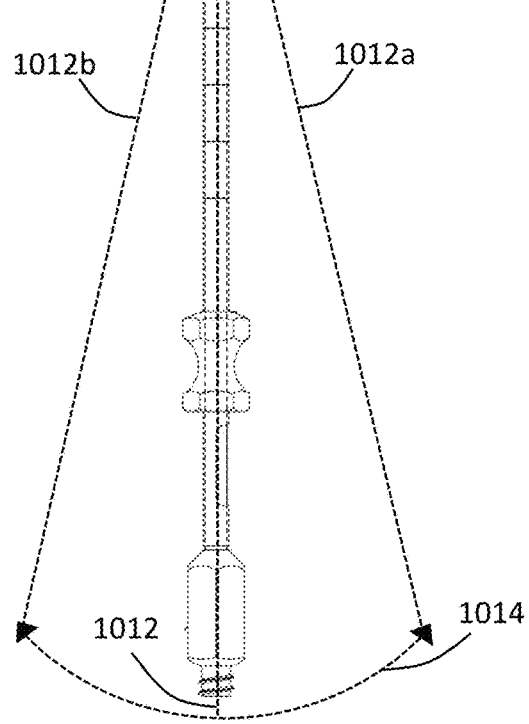
FIG. 11 shows a cut-away view of an illustrative staggered orientation of atraumatic subcutaneously inserted pellets.

With reference now to FIG. 11, there are shown medication pellets 104 delivered subcutaneously in the delivery area 1008 through the incision site 1002 on the skin and dermis of a patient from a cannula 200 inserted along the illustrative insertion path 1004. The swerving, curving, and weaving insertion path 1004 allows an assembled atraumatic insertion trocar to slip past various connective and fatty tissues without causing trauma, creating a linear space for the cannula 200. The connective and fatty tissues can variously include nerve tissue, blood vessels, arterioles, venuoles, capillaries, and lymphatic tissue. Upon removal of the cannula 200 during medication pellet 104 delivery, the connective and fatty tissues return toward their original position and pushing the delivered medication pellets 104 askew or off-kilter and effectively locking the medication pellets 104 in place in the subcutaneous tissue. Therefore, even though the medication pellets are extruded/delivered from the anterior opening of the cannula 200 along a linear path corresponding to the length of the linear cannula, the medication pellets arrive at final delivery positions within the subcutaneous tissue in a non-linear path as a result of the non-linear insertion path traversed by the assembled atraumatic insertion trocar 1010 during insertion. The final delivery positions of the medication pellets may form a delivery pattern along a delivery path that differs from the insertion path taken by the assembled atraumatic insertion trocar. The delivery path runs from the delivery site, where the anterior rounded tip of the insertion obturator reached at insertion full and where a first medication pellet may be deposited, along a trail formed by the sequentially deposited medication pellets to the incision through which the insertion obturator entered the patient's tissue.

In an alternative embodiment, the non-linear swerving, curving, and/or weaving insertion path 1004 may displace various connective, fatty, and other tissues without causing trauma such that deposited medication pellets are aligned in a linear or near linear pattern (i.e., deposition path) due to the accumulated action and force of the displaced tissues returning toward their original position around the deposited medication pellets.

Figure 12:
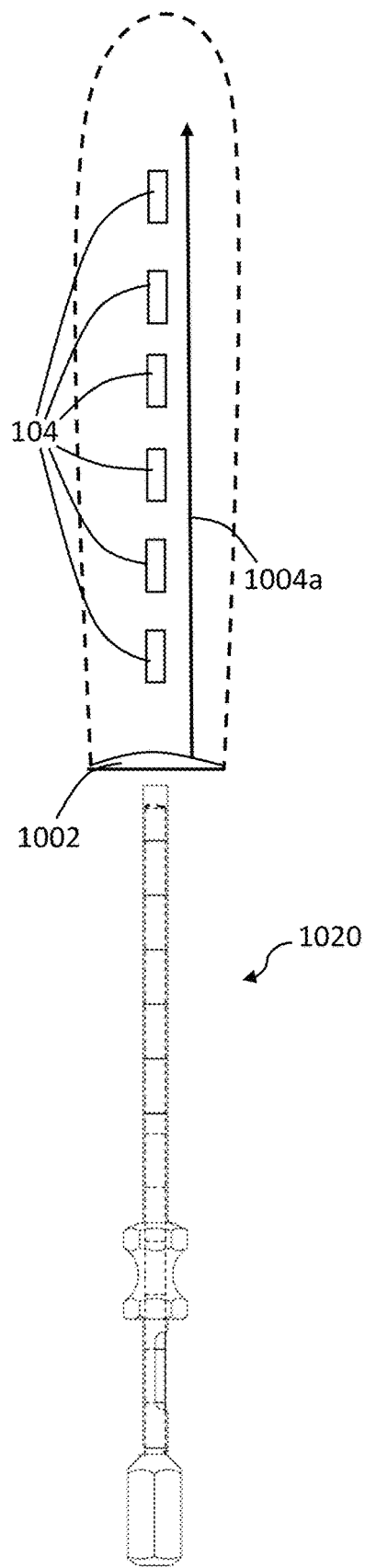
FIG. 12 shows a cut-away view of an illustrative orientation of atraumatic subcutaneously inserted pellets and assembled delivery trocar.

Referring now to FIG. 12, there are shown medication pellets 104 delivered through the incision site 1002 along a linear insertion path 1004a and an assembled atraumatic delivery trocar 1020. Medication pellets 104 may be spaced evenly, irregularly, or in groups (i.e., two medication pellets close together, adjacent, or abutting, two other medication pellets similarly close to one another but relatively further from the first two medication pellets, and so on). These groups may be of two or more pellets each. Although FIG. 12 shows medication pellets deposited in a nearly perfect linear orientation, the medication pellets may only be in approximately a linear orientation with one or more of the medication pellets being deposited slightly off of the linear centerline.

Figure 13:
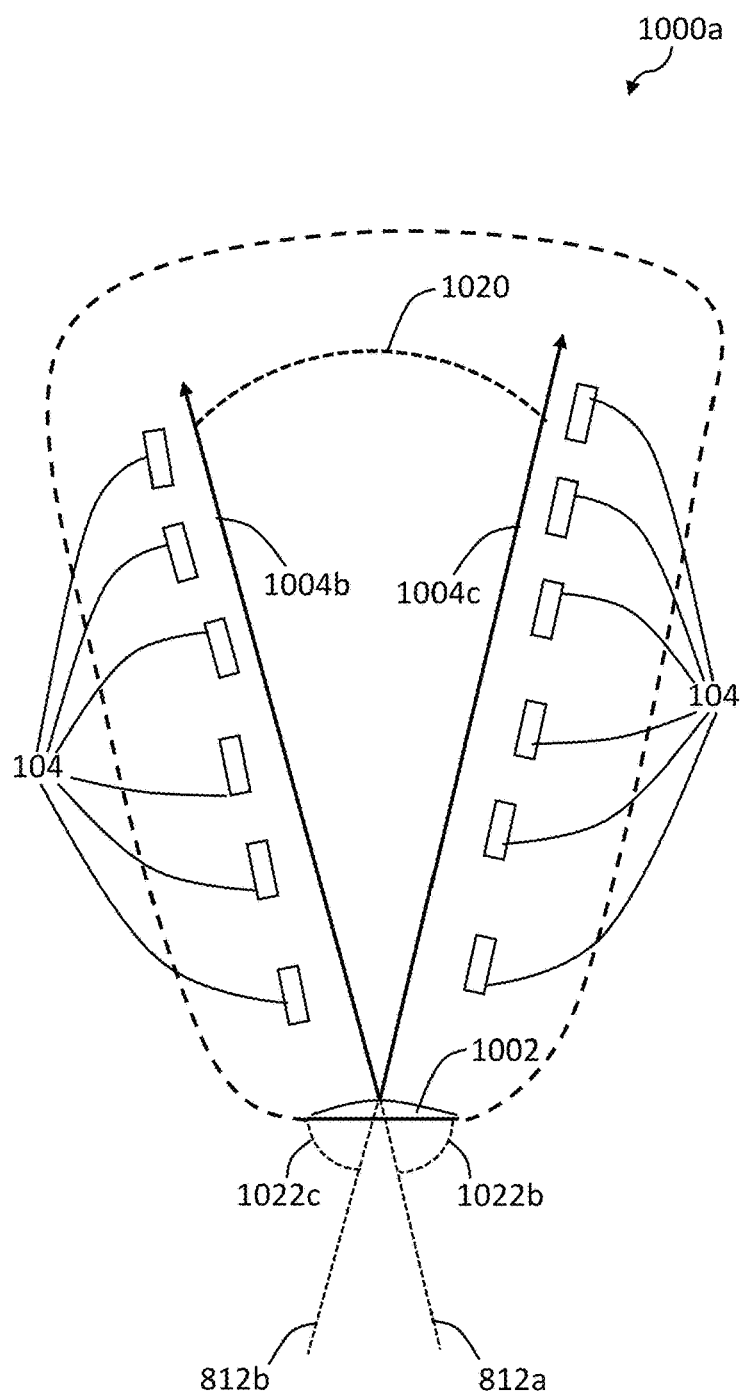
FIG. 13 shows a cut-away view of an illustrative orientation of two groups of atraumatic subcutaneously inserted pellets.

With reference to FIG. 13, there is shown an insertion area 1000a containing two sets of delivered medication pellets 104, wherein the medication pellets 104 are delivered along separate insertion paths 1004c and 1004b. The separate insertion paths 1004b and 1004c are separated by an angular distance 1020 corresponding to the angle 1022c or 1022b at which the centerline 1012a and 1012b of the assembled atraumatic insertion trocar (not shown) was inserted into the incision site 1002 and the assembled atraumatic delivery trocar (not shown) was removed. The angles 1022c and 1022b may be equal or not equal, and may range from a value of 0° through 360°. Thus, the separate insertion paths 1004b and 1004c form a fan arrangement, and in some embodiments multiple insertion paths may be made between or outside of the insertion paths 1004b and 1004c. Although the medication pellets of insertion paths 1004b and 1004c are only approximately linearly deposited, they may each be perfectly or near perfectly linearly deposited. Further, the insertion paths 1004b and 1004c are limited to linear embodiments, and may include curved, oscillating, and other non-linear paths.

Referring now to FIGS. 14A-C, there is shown an atraumatic method of subcutaneous medication delivery 1400. The method begins at step 1402 by making an incision at an insertion site 1002. The incision can be made with a scalpel or other cutting edge. In some embodiments, the incision is made by the punch scalpel 700.

The method continues at step 1404, by combining the cannula 200 and insertion obturator 220 to form the atraumatic insertion trocar 1010. The rounded tip 224 of the insertion obturator 220 is inserted into the posterior cannula opening 206, through the interior passage the cannula 200, so that the rounded tip 224 extends out through the anterior cannula opening 204. In a further embodiment, the insertion obturator 220 is inserted into the posterior cannula opening 206 so that the tab 232 on the insertion obturator 220 interfaces with the notch 212 on the tubular cannula body 202, and causes the assembled atraumatic insertion trocar 1010 to rotate about the centerline 1012 as a single unit, i.e. rotating the insertion obturator handle 230 causes the cannula 200 to rotate the same amount, and rotating the cannula handle 210 causes the insertion obturator 220 to rotate the same amount as well.

At step 1406 the assembled atraumatic insertion trocar 1010 is inserted into the incision site 1002 that is also termed an insertion site. The anterior rounded tip 224 of the insertion obturator 220 and thus, the assembled atraumatic insertion trocar 1010, enters the incision 1002 or insertion site, followed by the remaining portions of the atraumatic insertion trocar 1010 as described further below.

At step 1408 the incision 1002 or insertion point is probed with the assembled atraumatic insertion trocar 1010 along an insertion path to a predetermined insertion length. In various embodiments, the assembled trocar 1010 delivers a particular agent (i.e., a numbing solution, anesthetic, and/or hydrodissection fluid) to the tissue along the insertion path through openings in the insertion obturator. One of these openings may be located at or comprise the most anterior portion of the anterior blunt tip of the insertion obturator, so that the delivered agent is the first element of the assembled atraumatic insertion trocar to contact tissues along the insertion path. Alternatively or in addition to this configuration, the insertion obturator may include one or more openings proximal to the anterior rounded tip that deliver the agent to tissues adjacent to the anterior rounded tip and the tubular body of the insertion obturator and tubular cannula body. The delivered agent effectively lubricates the passage of the assembled atraumatic insertion obturator by creating a fluid buffer around the assembled atraumatic insertion obturator and gently separating the various tissues encountered by the assembled atraumatic insertion obturator during probing along an insertion path. This lubricating effect softens and hydrates tissues encountered, easing and improving the maneuverability of the atraumatic trocar within the tissue.

In these embodiments, the numbing solution may be delivered through only two openings proximate to the anterior rounded tip 224 of the insertion obturator, or through openings that spiral along the length of the portion of the insertion obturator tubular body that extends beyond the anterior opening of the cannula. The inventor hypothesizes that the numbing solution creates a fluid channel about the assembled atraumatic insertion trocar 1010, and thereby atraumatically enlarges the space or cavity of the delivery site and facilitates delivery of the medication pellets.

The insertion path may be linear or non-linear, and one or more insertion paths may originate at the same insertion/incision site and be angled away from one another in a fan-like orientation to allow the delivery of more medication pellets through a single incision. FIG. 12 demonstrates a linear insertion path 1004a followed by the assembled atraumatic insertion trocar under the direction of a doctor or other medical professional, FIG. 13 demonstrates angled insertion paths 1004b and 1004c, and FIGS. 10 and 11 demonstrate an oscillating insertion path 1004. An insertion path may only be angled with respect to another insertion path passing through the same incision or insertion site 1002 as the first insertion path. An oscillating insertion path 1004 may be achieved by directing the posterior portion of the assembled atraumatic insertion trocar 1010 in a side-to-side fashion. The side-to-side, wiggle-waggle, weaving, and/or oscillating motion operates to pass the rounded tip 224 around and past connective tissues in the subcutaneous tissue.

In operation, a doctor or assistant gently pushes the assembled atraumatic insertion trocar 1010 along an insertion path, moving the posterior portion of the assembled atraumatic insertion trocar 1010 to one side or the other as the doctor or operator feels resistance from connective tissues and fatty tissues impeding the passage of the atraumatic insertion trocar 1010 along the insertion path. The predetermined length to which the insertion path is probed may be measured by observing the deformation or bulging of the outer dermis layer caused by the passage of the atraumatic insertion trocar 1010 passing through the various subcutaneous tissues, i.e. fatty tissue, connective tissue, capillaries, venuoles, arterioles, nerves, etc. In other embodiments, the predetermined length may be measured using the cannula markings 214. Using the cannula markings 214 ensures that the insertion length is sufficient that all of the later loaded medication pellets 104 can be deposited within the subcutaneous tissue or to ensure that the medication pellets 104 are deposited a desired distance from the incision 1002 or insertion site.

In one embodiment, one or more numbing solutions, such as anesthetics, are administered through one or more openings 228 in the insertion obturator 220 while the assembled atraumatic insertion trocar 1010 probes along the insertion path. In another embodiment, anesthetics are administered through two openings located in the anterior portion of the insertion obturator 220 proximate to the anterior rounded tip 224 while the assembled atraumatic insertion trocar 1010 probes along the insertion path. By way of example and not of limitation, the numbing solution may include a combination of a saline solution, lidocaine and epinephrine; the numbing agent is lidocaine and the epinephrine constricts the blood vessels to minimize bleeding. In addition to numbing the tissue surrounding the insertion path during insertion of the assembled atraumatic insertion trocar, the numbing solution may act as a hydrodissection fluid that lubricates the assembled atraumatic insertion trocar's passage into the various tissues by gently hydrating, softening, and displacing tissues from the insertion path.

At step 1410, the insertion obturator 220 is removed from the cannula 200 and the incision 1002. In one embodiment, the cannula 200 is kept in position, while the insertion obturator 220 is removed. The cannula 200 may be kept in position by holding the cannula handle 210 while the insertion obturator handle is used to remove the insertion obturator 220.

At step 1412, a medication pellet 104 is loaded into the interior passage of the cannula 200 through the medication slot 208. In one embodiment, the loaded medication pellet is pushed toward the anterior opening 204 at the anterior end of the cannula 200 with the delivery obturator 240, but not through the anterior opening 204. In another embodiment, the loaded medication pellet is pushed toward the anterior opening 204 at the anterior end of the cannula 200 and through the anterior opening 204.

At decision diamond 1414, a next medication pellet may be loaded into the interior passage of the cannula 200 in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula 200, the most recently loaded medication pellet is pushed toward the anterior opening 204 at the anterior end of the cannula 200 with the delivery obturator 240. Any next or subsequently loaded medication pellets are pushed through the cannula 200 so that none of the previously loaded medication pellets are extruded through the anterior opening 204 at the anterior end of the cannula 200 and delivered to a delivery area 1008.

At step 1416, the desired number of medication pellets 104 have been loaded into the interior passage of the cannula 200, and the blunt tip 244 of the delivery obturator 240 is inserted into the posterior opening 206 of the cannula 200. The blunt tip 244 of the delivery obturator 240 is passed through the interior passage of the cannula 200 to abut the most posterior loaded medication pellet 104 and push all pellets into a desired position. In one embodiment, the desired position for the medication pellets is as depicted in FIG. 9B, where the loaded pellets 104 pressed to abut one another and align with the cannula markings 214, as well as the anterior opening 204 of the cannula 200.

Figure 1A:
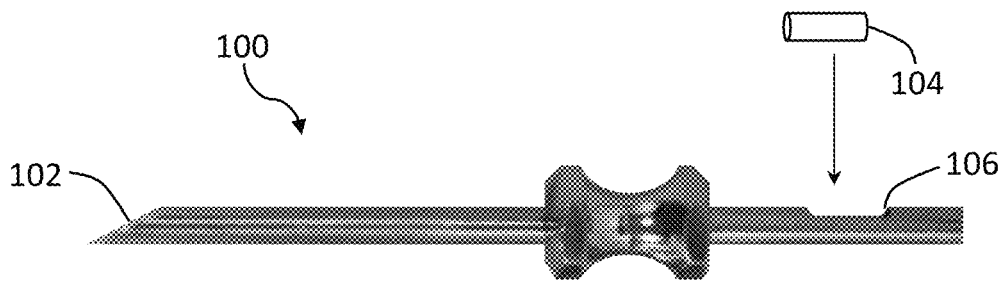
FIG. 1A shows a prior art trocar cannula.
Figure 1B:
FIG. 1B shows a prior art trocar insertion obturator.
Figure 1C:
FIG. 1C shows a prior art trocar delivery obturator.
Figure 1D:
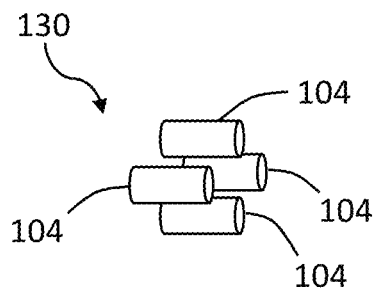
FIG. 1D shows a side view of a prior art radial pellet clump.
Figure 1E:
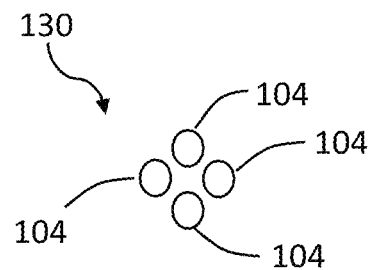
FIG. 1E shows a front view of a prior art radial pellet clump.

At step 1418, the loaded medication pellet(s) 104 are extruded through the anterior opening 204 of the cannula 200 and delivered to a subcutaneous delivery area 1008. In one embodiment, the cannula 200 is slowly removed from the incision 1002 as the delivery obturator 240 (alternatively the insertion obturator may be used instead) is inserted further into the interior passage of the cannula 200. By slowly removing the cannula 200 during insertion of the delivery obturator 240, the delivery site 1006 for each successive medication pellet is shifted closer to the incision 1002 or insertion site. Moving the delivery site 1006 of successive pellets allows the medication pellets to be delivered in a linear formation as in FIG. 12, or a snaking, winding or "staggered" formation as in FIG. 11, as opposed to the radial clump 130 of the prior art in FIG. 1D. Thus, simultaneous removal of the cannula 200 and insertion or depression of the delivery obturator 240 forces successive medication pellets out of the cannula 200 into a delivery site that is unique for each medication pellet.

At step 1420, the assembled atraumatic delivery trocar 1020 is retracted along the insertion path toward the incision 1002 or insertion site. In one embodiment, at least an anterior portion of the cannula 200 remains within the incision 1002 or insertion site. Notably, whether the atraumatic insertion trocar 1010 was inserted along a linear path as in FIGS. 12 and 13, or a snaking path as in FIG. 10, the corresponding atraumatic delivery trocar 1020 is removed directly, i.e. without any snaking, wiggling, or wagging, such that the removal of the atraumatic delivery trocar 1020 follows a linear or approximately linear path. In other words, no matter the type of insertion path, the atraumatic delivery trocar 1020 is retracted with a linear motion along a linear path. As described above, when the insertion path is non-linear, displaced tissue resumes its approximate original location and locks one or more delivered medication pellets in place in the subcutaneous tissue. When the insertion path is linear, tissue may still contract about the delivered medication pellet(s) to hold them in place, although the force of this holding action may be less than when a non-linear insertion path is used.

At step 1422, the delivery obturator 240 is removed from the cannula 200. At decision diamond 1424, a doctor or assistant may determine whether to proceed with a second or next insertion or whether to begin terminating the method. If termination is elected, the method proceeds to step 1442 where the cannula 200 or assembled atraumatic delivery trocar 1020 is removed from the incision 1002 or the insertion site; the incision 1002 is closed and the method ends. If a second or next insertion is elected, the method proceeds to step 1426.

At step 1426, the method proceeds by again combining the cannula 200 and the insertion obturator 220 to form the atraumatic insertion trocar 1010. Since at least an anterior portion of the cannula 200 remains within the incision 1002 or insertion site, when the insertion obturator 220 is inserted into the interior passage of the cannula the rounded tip 224 emerges from the anterior opening 204 of the cannula 200 directly into subcutaneous tissue within the incision 1002 or insertion site. In a further embodiment, the insertion obturator 220 is inserted into the posterior cannula opening 206 so that the tab 232 on the insertion obturator 220 interfaces with the notch 212 on the tubular cannula body 202.

At step 1428, the assembled insertion trocar 1010 is angled away from the previous insertion path, as with the insertion paths 1004b and 1004c in FIG. 13, towards a next or second insertion path. The assembled insertion trocar 1010 is then used to probe along the length of the next or second insertion path to a predetermined insertion length. This predetermined insertion length may be dependent on the number of medication pellets to be delivered, i.e. a longer insertion length may be desired when more medication pellets are to be delivered. However, it should be noted that even just a single medication pellet may be inserted along an insertion path that is same length as the insertion path for several pellets. As with the initial insertion path, the second insertion path can be linear or oscillating, but must be angle away from the initial insertion path.

At step 1430, as with step 1410, the insertion obturator 220 is removed from the cannula 200 and the incision 1002 or insertion site, while keeping the cannula 200 in place within the incision 1002 or insertion point.

At step 1432, as with step 1412, a medication pellet 104 is loaded into the interior passage of the cannula 200 through the medication slot 208. In one embodiment, only one medication pellet is loaded into the medication slot.

At decision diamond 1434, as with decision diamond 1412, a next medication pellet may be loaded into the interior passage of the cannula 200 in the same fashion as the first medication pellet, or the method may proceed to step 1434.

At step 1436, as with step 1416, the desired number of medication pellets 104 have been loaded into the interior passage of the cannula 200, and the blunt tip 244 of the delivery obturator 240 is inserted into the posterior opening 206 of the cannula 200. The blunt tip 244 of the delivery obturator 240 is passed through the interior passage of the cannula 200 to abut the most posterior loaded medication pellet 104 and push all pellets into a desired position.

At step 1438, as with step 1418, the loaded medication pellet(s) 104 are extruded through the anterior opening 204 of the cannula 200 and delivered to a second subcutaneous delivery area.

At step 1440, as with step 1420, the assembled atraumatic delivery trocar 1020 is retracted along the insertion path toward the incision 1002 or insertion site. In one embodiment, at least an anterior portion of the cannula 200 remains within the incision 1002 or insertion site, allowing the method to either terminate at step 1442 or return to decision diamond 1424.

At step 1442, the cannula 200 or assembled atraumatic delivery trocar 1020 is removed from the incision 1002 or the insertion site; the incision 1002 is closed and the method ends.

With reference now to FIG. 15, there is shown an alternative method of atraumatic subcutaneous pellet delivery 1500 that does not use the delivery obturator as in the method of FIG. 14. The method begins at step 1502 by combining the cannula 200 and an insertion obturator to form an atraumatic insertion trocar. The rounded tip 224 of the insertion obturator is inserted into the posterior cannula opening 206, through the interior passage the cannula 200, so that the rounded tip 224 extends out through the anterior cannula opening 204. In a further embodiment, the insertion obturator is inserted into the posterior cannula opening 206 so that at least one tab 232 on the insertion obturator interfaces with at least one notch 212 on the tubular cannula body 202, and causes the assembled atraumatic insertion trocar to rotate about the centerline 1012 as a single unit, i.e. rotating the insertion obturator causes the cannula 200 to rotate the same amount, and rotating the cannula causes the insertion obturator to rotate the same amount as well. In an alternative embodiment, the insertion obturator does not include any tabs and the tubular cannula body 202 does not include any notches. Instead, in this alternative embodiment a cap, stopper, or flange at the posterior end of the insertion obturator abuts the posterior cannula opening 206 to prevent the insertion obturator from passing entirely through the interior of the cannula tubular body.

At step 1504 the assembled atraumatic insertion trocar is inserted into an incision site 1002. The anterior rounded tip 224 of the insertion obturator and thus, the assembled atraumatic insertion trocar, enters the incision 1002, followed by the remaining portions of the atraumatic insertion trocar as described further below.

At step 1506 the incision 1002 is probed with the assembled atraumatic insertion trocar along an insertion path to an insertion length.

In operation, an operator pushes the assembled atraumatic insertion trocar along an insertion path, sliding the anterior rounded tip of the assembled atraumatic insertion trocar 224 past connective tissues and fatty tissues impeding the passage of the atraumatic insertion trocar as the operator feels resistance. The length or depth to which the atraumatic insertion trocar is probed or inserted into the incision 1002 may be measured by observing the deformation or bulging of the outer dermis layer caused by the passage of the atraumatic insertion trocar through the various subcutaneous tissues. In other embodiments, the length or depth of insertion may be measured using the cannula markings 214.

At step 1508, the insertion obturator is removed from the cannula 200, and the insertion obturator is removed from the incision 1002. The cannula 200 is kept in position, while the insertion obturator is removed. The cannula 200 may be kept in position by holding a cannula handle 210 while an insertion obturator handle is used to remove the insertion obturator.

At step 1510, a medication pellet 104 is loaded into the interior passage of the cannula 200 through the medication slot 208. In one embodiment, the loaded medication pellet is pushed toward the anterior opening 204 at the anterior end of the cannula 200 with the insertion obturator, but not through the anterior opening 204. This may be accomplished using markings on the insertion obturator that correspond to the medication length and the markings 214 on the cannula. In another embodiment, the loaded medication pellet is pushed toward the anterior opening 204 at the anterior end of the cannula 200 and through the anterior opening 204 with the insertion obturator.

At decision diamond 1512, a next medication pellet may be loaded into the interior passage of the cannula 200 in the same fashion as the first medication. The next medication pellet 104 can be a second, third, fourth, fifth, sixth, etc. medication pellet depending on the number of previously loaded medication pellets and the relative length of the cannula 200. In one embodiment, when a next pellet is loaded into the interior passage of the cannula 200, the most recently loaded medication pellet is pushed toward the anterior opening 204 at the anterior end of the cannula 200 with the insertion obturator. Any next or subsequently loaded medication pellets are pushed through the cannula 200 so that none of the previously loaded medication pellets are extruded through the anterior opening 204 at the anterior end of the cannula 200 and delivered to a delivery area 1008.

At step 1514, the desired number of medication pellets 104 have been loaded into the interior passage of the cannula 200, and the blunt or anterior rounded tip 224 of the insertion obturator is reinserted into the posterior opening 206 of the cannula 200. The anterior rounded tip 224 of the insertion obturator is passed through the interior passage of the cannula 200 to abut the most posterior loaded medication pellet 104 and push all pellets into a desired position.

At step 1516, the loaded medication pellet(s) 104 are extruded through the anterior opening 204 of the cannula 200 and delivered to a subcutaneous delivery area 1008. In one embodiment, the cannula 200 is removed from the incision 1002 as the insertion obturator is inserted further into the interior passage of the cannula 200. By removing the cannula 200 during insertion of the insertion obturator, the delivery site 1006 for each successive medication pellet is shifted closer to the incision 1002 or insertion site. Thus, the medication pellets are delivered in a linear formation as in FIG. 12, or a snaking, winding or "staggered" formation as in FIG. 11. Thus, simultaneous removal of the cannula 200 and insertion or depression of the insertion obturator forces successive medication pellets out of the cannula 200 into a delivery site that is unique for each medication pellet.

At step 1518, the assembled atraumatic trocar is retracted linearly back through the incision 1002, the incision 1002 is closed and the method ends. In one embodiment, at least an anterior portion of the atraumatic trocar remains within the incision 1002 to allow reinsertion along a second insertion path beginning at the incision 1002 for delivery of a second set of pellets.

Referring now to FIGS. 16A and 16B, there is shown an illustrative method of using an atraumatic trocar kit to subcutaneous deliver medication pellets. The method begins at step 1602 by opening a package containing an atraumatic trocar kit. In one embodiment, the atraumatic trocar kit is disposable and contains a disposable insertion obturator 500, a disposable cannula 520, and a punch scalpel 700. In further embodiments, the atraumatic trocar kit also includes a disposable delivery obturator 510, as well as instructions informing a user on how to assemble the disposable trocar and deliver pellets to a subcutaneous delivery site, scissors, bandages, and antiseptic ointments.

The method continues at step 1604 by making an incision at an insertion site using the punch scalpel 700. In operation the punch scalpel base 708 is placed on a patient's skin at an insertion site. The scalpel blade 704 is then pressed or plunged into the patient's skin to an incision depth. The incision depth is limited by the punch scalpel bracket. In on embodiment the scalpel blade is plunged into the patient's skin using a scalpel handle attached to the scalpel blade 700. The incision width is limited to the width of the scalpel blade 704. In another embodiment, the operator confirms that the scalpel blade 704 is aligned with the desired insertion site by positioning one or more guide notches 712 at the desired insertion site.

At step 1606, the cannula and insertion obturator are combined to form the atraumatic insertion trocar. The rounded tip of the insertion obturator is inserted into the posterior cannula opening, through the interior passage the cannula, so that the rounded tip extends out through the anterior cannula opening. In a further embodiment, the insertion obturator is inserted into the posterior cannula opening so that the tab on the insertion obturator interfaces with the notch on the tubular cannula body, and causes the assembled atraumatic insertion trocar to rotate about a centerline as a single unit.

At step 1608, the assembled atraumatic insertion trocar is inserted into the incision site 1002. The anterior rounded tip of the insertion obturator, and thus, the assembled atraumatic insertion trocar, enters the incision 1002 followed by the remaining portions of the atraumatic insertion trocar.

At step 1610, the incision 1002 is probed with the assembled atraumatic insertion trocar along an insertion path to an insertion length. In various embodiments, the assembled trocar delivers a numbing solution or anesthetic to the tissue along the insertion path through openings in the insertion obturator.

At step 1612, the insertion obturator is removed from the cannula and the incision 1002. In one embodiment, the cannula is kept in position, while the insertion obturator is removed. The cannula may be kept in position by holding a cannula handle while an insertion obturator handle is used to remove the insertion obturator.

At step 1614, a medication pellet 104 is loaded into the interior passage of the cannula through a medication slot of the cannula. In one embodiment, the loaded medication pellet is pushed toward the anterior opening at the anterior end of the cannula with the delivery obturator, but not through the anterior opening.

At decision diamond 1616, a next medication pellet may be loaded into the interior passage of the cannula in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula, the most recently loaded medication pellet is pushed toward the anterior opening at the anterior end of the cannula with the delivery obturator. Any next or subsequently loaded medication pellets are pushed through the cannula so that none of the previously loaded medication pellets are extruded through the anterior opening at the anterior end of the cannula and delivered to a delivery area 1008.

At step 1618, the desired number of medication pellets 104 have been loaded into the interior passage of the cannula, and the blunt tip of the delivery obturator is inserted into the posterior opening of the cannula. The blunt tip of the delivery obturator is passed through the interior passage of the cannula to abut the most posterior loaded medication pellet 104 and push all pellets into a desired position.

At step 1620, the loaded medication pellet(s) 104 are extruded through the anterior opening of the cannula and delivered to a subcutaneous delivery area 1008. In one embodiment, the cannula is removed from the incision 1002 as the delivery obturator is inserted further into the interior passage of the cannula. By removing the cannula during insertion of the delivery obturator, the delivery site 1006 for each successive medication pellet is shifted closer to the incision 1002 or insertion site. Thus, simultaneous removal of the cannula and insertion or depression of the delivery obturator forces successive medication pellets out of the cannula into a delivery site that is unique for each medication pellet.

At step 1622, the assembled atraumatic delivery trocar is removed from the incision 1002, the components of the atraumatic trocar kit are disposed of, and the method is terminated.

In further embodiments, the pellet dosage of a target compound, i.e. testosterone, estrogen, progesterone, is determined in relation to a baseline measurement of the target compound in the patient's blood stream. The baseline measurement is determined prior to atraumatic delivery of medication pellets. The efficacy of the selected dosage is then determined by measuring the amount of the compound per volume, termed a compound level, in the patient's bloodstream at various time periods after subcutaneous insertion of the medication pellets. In various embodiments, the compound level is measured one week, one month, three months, and six months after atraumatic pellet delivery. In other embodiments, the compound level is measured weekly, biweekly, or monthly. Later atraumatic pellet delivery doses are then adjusted, i.e. increased or decreased, depending on whether the compound levels resulting from a previous atraumatic delivery were higher or lower than desired.

In an exemplary embodiment, normal testosterone blood levels range from 400 to 1,200 nanograms/deciliter (ng/dl), but a patient's testosterone baseline level is measured at 50 ng/dl. One week after atraumatically delivering one 200 mg pellet of testosterone, the patient's testosterone level is measured at 60 ng/dl, one month after atraumatic delivery the patient's testosterone level is measured at 100 ng/dl, and three months after atraumatic delivery the patient's testosterone level is measured at 105 ng/dl. This feedback may suggest to a doctor or operator that a subsequent atraumatically delivered pellet dosage should be increase to two, three, four, or more 200 mg pellets. This method of baseline measurement, followed by post-delivery measurement accounts for the differences in patient body composition, activity level, and metabolism, which vary significantly and affect pellet dissolution into the blood stream.

The atraumatic trocar apparatus, system and method described above may be used to deliver medication pellets into subcutaneous tissue with little, minimal, or no damage to the subcutaneous tissue. The inventor hypothesizes that the atraumatic insertion and subcutaneous delivery of medication pellets improves the absorption rate of the medication pellets over prior art trocar apparatuses by limiting or eliminating trauma, such as laceration to nerves, arterioles, venuoles, capillaries, or fat cell membrane punctures, which results in cellular death and may cause the formation of chronic collagenous scar tissue.

Further, the inventor hypothesizes that the atraumatic method of pushing aside and slipping past connective and fatty tissue with the rounded tip of the insertion obturator allows the connective and fatty tissue to move or pop back toward their original position as the trocar is removed from the insertion path and incision. As the connective and fatty tissue moves, slides, or pops back toward its original position, the connective and fatty tissues have the effect of locking or blocking the delivered medication pellets in place.

Further still, the inventor hypothesizes that the locking or blocking action of the connective and fatty tissue prevents or limits the likelihood that the delivered medication pellets are inadvertently extruded from the subcutaneous tissue because of pressure, a fall, or other stress.

The inventor further hypothesizes that the atraumatic insertion and subcutaneous delivery of medication pellets allows the incision made to insert the medication pellets to heal more quickly and decrease the likelihood that a subcutaneously delivered or inserted medication pellet is inadvertently extruded from the subcutaneous tissue because of pressure, a fall, or other stress.

Additionally, the inventor hypothesizes that the reduced inflammation caused by the atraumatic trocar apparatus and methods reduce the degree and incidence of scarring at the incision site.

Whereas invasive, traumatic prior art methods of subcutaneous pellet insertion cause blood to pool around the traumatized delivery site due to local destruction of fatty tissue, the presently disclosed systems and methods of atraumatic subcutaneous pellet delivery allows pellets to sit in a layer of fatty tissue with no abnormal blood or lymph fluids surrounding the delivered pellets. Destruction of fatty tissue from the traumatic prior art methods cause inflammation and/or pain, which is undesirable both because of pain's effect on the patient's psyche and because local inflammatory cytokines create a milieu that poorly dissolves medication pellets, or fails to dissolve medication pellets entirely. The inventors hypothesize that this atraumatic delivery allows the pellets to be recognized earlier by the body and absorbed more quickly, predictably, and deliberately as a result, and as compared to traumatic insertion.

It is to be understood that the detailed description of illustrative embodiments are provided for illustrative purposes. Thus, the apparatus, system, kit and method presented above may evolve to benefit from the improved performance and lower cost of the future hardware components that meet the system and method requirements presented. The scope of the claims is not limited to these specific embodiments or examples. Therefore, various process limitations, elements, details, and uses can differ from those just described, or be expanded on or implemented using technologies or materials not yet commercially viable, and yet still be within the inventive concepts of the present disclosure. The scope of the invention is determined by the following claims and their legal equivalents.

What is claimed is:

1. A method for delivering two or more medication pellets through an incision to a subcutaneous tissue comprising:
   receiving an obturator in a tubular cannula body, wherein the obturator includes an anterior rounded tip and a tubular obturator body, wherein the cannula includes the tubular cannula body having an anterior end with an anterior opening, a posterior end with a posterior opening, and a medication slot disposed along the tubular cannula body;
   passing the obturator through the tubular cannula body so that the anterior rounded tip of the obturator extends past the anterior end of the tubular cannula body;
   probing, with the cannula and the obturator, the incision into the subcutaneous tissue along an insertion path within the subcutaneous tissue up to an insertion length;
   removing the obturator from the tubular cannula body;
   placing the two or more medication pellets in the medication slot;
   receiving the obturator at the posterior opening of the tubular cannula body;
   passing, by the anterior rounded tip of the obturator, the two or more medication pellets through the tubular cannula body so that the obturator pushes the two or more medication pellets through the tubular cannula body, the two or more medication pellets exit the anterior opening of the tubular cannula body, and the two or more medication pellets enter a delivery site;
   aligning a first medication pellet and a second medication pellet of the two or more medication pellets along a non-linear delivery path between the delivery site and the incision.

2. The method of claim 1 further including probing, the cannula and the obturator, along the insertion path in a side-to-side pattern.

3. The method of claim 1 wherein the cannula includes a cannula handle fixedly coupled to the cannula; and
   the obturator includes an obturator handle fixedly coupled to the obturator.

4. The method of claim 1 further including probing, with the cannula and the obturator, along the insertion path in an irregular pattern.

5. The method of claim 1 further including:
   aligning the cannula and the obturator along a second insertion path;
   passing the obturator through the tubular cannula body so that the anterior rounded tip of the obturator extends past the anterior end of the tubular cannula body;

probing, with the cannula and the obturator, the incision into the subcutaneous tissue along the second insertion path within the subcutaneous tissue up to an insertion length;

removing the obturator from the tubular cannula body;

placing a second set of two or more medication pellets in the medication slot;

receiving the obturator at the posterior opening of the tubular cannula body;

passing, by the anterior rounded tip of the obturator, the second set of two or more medication pellets through the tubular cannula body so that the obturator pushes the second set of two or more medication pellets through the tubular cannula body, the second set of two or more medication pellets exit the anterior opening of the tubular cannula body, and the second set of two or more medication pellets enter a second delivery site; and aligning a first medication pellet and a second medication pellet of the second set of two or more medication pellets along a second non-linear delivery path between the second delivery site and the incision.

6. A method for delivering two or more medication pellets through an incision to a subcutaneous tissue comprising:

receiving an obturator in a tubular cannula body, wherein the obturator includes an anterior blunt tip and a tubular obturator body, wherein the cannula includes the tubular cannula body having an anterior end with an anterior opening, a posterior end with a posterior opening, and a medication slot disposed along the tubular cannula body;

passing the obturator through the tubular cannula body so that the anterior blunt tip of the obturator extends past the anterior end of the tubular cannula body;

probing, with the cannula and the obturator, the incision into the subcutaneous tissue along an insertion path within the subcutaneous tissue up to an insertion length;

removing the obturator from the tubular cannula body;

placing the two or more medication pellets in the medication slot;

receiving the obturator at the posterior opening of the tubular cannula body;

passing, by the anterior blunt tip of the obturator, the two or more medication pellets through the tubular cannula body so that the obturator pushes the two or more medication pellets through the tubular cannula body, the two or more medication pellets exit the anterior opening of the tubular cannula body, and the two or more medication pellets enter a delivery site;

aligning a first medication pellet and a second medication pellet of the two or more medication pellets along a non-linear delivery path between the delivery site and the incision.

7. The method of claim 6 further including probing, the cannula and the obturator, along the insertion path in a side-to-side pattern.

8. The method of claim 6 wherein the cannula includes a cannula handle fixedly coupled to the cannula; and the obturator includes an obturator handle fixedly coupled to the obturator.

9. The method of claim 6 further including probing, with the cannula and the obturator, along the insertion path in an irregular pattern.

10. The method of claim 6 further including:

aligning the cannula and the obturator along a second insertion path;

passing the obturator through the tubular cannula body so that the anterior blunt tip of the obturator extends past the anterior end of the tubular cannula body;

probing, with the cannula and the obturator, the incision into the subcutaneous tissue along the second insertion path within the subcutaneous tissue up to an insertion length;

removing the obturator from the tubular cannula body;

placing a second set of two or more medication pellets in the medication slot;

receiving the obturator at the posterior opening of the tubular cannula body;

passing, by the anterior blunt tip of the obturator, the second set of two or more medication pellets through the tubular cannula body so that the obturator pushes the second set of two or more medication pellets through the tubular cannula body, the second set of two or more medication pellets exit the anterior opening of the tubular cannula body, and the second set of two or more medication pellets enter a second delivery site; and aligning a first medication pellet and a second medication pellet of the second set of two or more medication pellets along a second non-linear delivery path between the second delivery site and the incision.

11. A method for delivering two or more medication pellets through an incision to a subcutaneous tissue comprising:

receiving an obturator in a tubular cannula body, wherein the obturator includes an anterior rounded tip and a tubular obturator body, wherein the cannula includes the tubular cannula body having an anterior end, a posterior end, and a medication slot disposed along the tubular cannula body;

passing the obturator through the tubular cannula body so that the anterior rounded tip of the obturator extends past the anterior end of the tubular cannula body;

probing, with the cannula and the obturator, the incision into the subcutaneous tissue along an insertion path within the subcutaneous tissue up to an insertion length;

removing the obturator from the tubular cannula body;

placing the two or more medication pellets in the medication slot;

receiving, by the tubular cannula body having the two or more medication pellets placed therein, the obturator;

delivering, by the anterior rounded tip of the obturator, the two or more medication pellets to a delivery site by removing the cannula from the incision;

aligning a first medication pellet and a second medication pellet of the two or more medication pellets along a non-linear delivery path between the delivery site and the incision.

12. The method of claim 11 further including probing, the cannula and the obturator, along the insertion path in a side-to-side pattern.

13. The method of claim 11 wherein the cannula includes a cannula handle fixedly coupled to the cannula; and the obturator includes an obturator handle fixedly coupled to the obturator.

14. The method of claim 11 further including probing, with the cannula and the obturator, along the insertion path in an irregular pattern.

15. The method of claim 11 further including:

aligning the cannula and the obturator along a second insertion path;

passing the obturator through the tubular cannula body so that the anterior rounded tip of the obturator extends past the anterior end of the tubular cannula body;

probing, with the cannula and the obturator, the incision into the subcutaneous tissue along the second insertion path within the subcutaneous tissue up to an insertion length;

removing the obturator from the tubular cannula body;

placing a second set of two or more medication pellets in the medication slot;

receiving, by the tubular cannula body having the second set of two or more medication pellets placed therein, the obturator;

delivering, by the anterior rounded tip of the obturator, the second set of two or more medication pellets to a second delivery site by removing the cannula from the incision; and aligning a first medication pellet and a second medication pellet of the second set of two or more medication pellets along a second non-linear delivery path between the second delivery site and the incision.

16. A method for delivering two or more medication pellets through an incision to a subcutaneous tissue comprising:

receiving an obturator in a tubular cannula body, wherein the obturator includes an anterior blunt tip and a tubular obturator body, wherein the cannula includes the tubular cannula body having an anterior end, a posterior end, and a medication slot disposed along the tubular cannula body;

passing the obturator through the tubular cannula body so that the anterior blunt tip of the obturator extends past the anterior end of the tubular cannula body;

probing, with the cannula and the obturator, the incision into the subcutaneous tissue along an insertion path within the subcutaneous tissue up to an insertion length;

removing the obturator from the tubular cannula body;

placing the two or more medication pellets in the medication slot;

receiving, by the tubular cannula body having the two or more medication pellets placed therein, the obturator;

delivering, by the anterior blunt tip of the obturator, the two or more medication pellets to a delivery site by removing the cannula from the incision;

aligning a first medication pellet and a second medication pellet of the two or more medication pellets along a non-linear delivery path between the delivery site and the incision.

17. The method of claim 16 further including probing, the cannula and the obturator, along the insertion path in a side-to-side pattern.

18. The method of claim 16 wherein the cannula includes a cannula handle fixedly coupled to the cannula; and the obturator includes an obturator handle fixedly coupled to the obturator.

19. The method of claim 16 further including probing, with the cannula and the obturator, along the insertion path in an irregular pattern.

20. The method of claim 16 further including:

aligning the cannula and the obturator along a second insertion path;

passing the obturator through the tubular cannula body so that the anterior blunt tip of the obturator extends past the anterior end of the tubular cannula body;

probing, with the cannula and the obturator, the incision into the subcutaneous tissue along the second insertion path within the subcutaneous tissue up to an insertion length;

removing the obturator from the tubular cannula body;

placing a second set of two or more medication pellets in the medication slot;

receiving, by the tubular cannula body having the second set of two or more medication pellets placed therein, the obturator;

delivering, by the anterior blunt tip of the obturator, the second set of two or more medication pellets to a second delivery site by removing the cannula from the incision; and aligning a first medication pellet and a second medication pellet of the second set of two or more medication pellets along a second non-linear delivery path between the second delivery site and the incision.

* * * * *